US012672967B2

(12) United States Patent
Ren

(10) Patent No.: US 12,672,967 B2
(45) Date of Patent: Jul. 7, 2026

(54) DEXTEROUS HAND

(71) Applicant: NEUROCEAN TECHNOLOGIES INC., Shenzhen (CN)

(72) Inventor: Hualong Ren, Shenzhen (CN)

(73) Assignee: NEUROCEAN TECHNOLOGIES INC., Shenzhen (CN)

( * ) Notice: Subject to any disclaimer, the term of this patent is extended or adjusted under 35 U.S.C. 154(b) by 1071 days.

(21) Appl. No.: 17/831,046

(22) Filed: Jun. 2, 2022

(65) Prior Publication Data

US 2022/0287853 A1     Sep. 15, 2022

Related U.S. Application Data

(63) Continuation-in-part of application No. PCT/CN2020/133435, filed on Dec. 2, 2020.

(30) Foreign Application Priority Data

Dec. 2, 2019     (CN) .......................... 201911214168.1

(51) Int. Cl.
*A61F 2/70*          (2006.01)
*A61F 2/58*          (2006.01)
(Continued)

(52) U.S. Cl.
CPC .............. *A61F 2/586* (2013.01); *A61F 2/583* (2013.01); *A61F 2/585* (2013.01); *A61F 2/70* (2013.01);
(Continued)

(58) Field of Classification Search
CPC .......... A61F 2/586; A61F 2/583; A61F 2/585; A61F 2/70; A61F 2002/5001; B25J 15/10
(Continued)

(56) References Cited

U.S. PATENT DOCUMENTS 2,847,678 A * 8/1958 Opuszenski .............. A61F 2/58
623/64
8,483,880 B2 * 7/2013 de la Rosa Tames ......................
B25J 15/0009
600/595
(Continued)

FOREIGN PATENT DOCUMENTS

CN        104382674 A      3/2015
CN        107972022 A      5/2018
(Continued)

OTHER PUBLICATIONS

International Search Report for International Application No. PCT/CN2020/133435; Date of Completion: Feb. 5, 2021; Date of Mailing: Mar. 3, 2021; 5 Pages.
(Continued)

*Primary Examiner* — Paul T Chin
(74) *Attorney, Agent, or Firm* — CANTOR COLBURN LLP

(57)          ABSTRACT

A dexterous hand, including a hand module, the hand module includes one or more finger units and a palm unit, wherein each finger unit includes a plurality of phalanges and one or more interphalangeal joints, wherein the palm unit includes a carpometacarpal base, one or more metacarpals, one or more carpometacarpal joints, and one or more metacarpophalangeal joint, wherein each finger unit is hinged to a respective metacarpal by a respective metacarpophalangeal joint, wherein each metacarpal is respectively connected to the carpometacarpal base, wherein each interphalangeal joint has degrees of freedom of flexion extension, wherein each metacarpophalangeal joint has degrees of freedom of flexion extension, degrees of freedom of abduction adduction and degrees of freedom of circumduction, wherein each interphalangeal joint's degrees of freedom of flexion extension, each metacarpophalangeal joint's degrees
(Continued)

of freedom of flexion extension, each metacarpophalangeal joint's degrees of freedom of abduction adduction are driven by different actuators.

46 Claims, 6 Drawing Sheets

(51) Int. Cl.
    *B25J 15/10*         (2006.01)
    *A61F 2/50*         (2006.01)
    *A61F 2/54*         (2006.01)

(52) U.S. Cl.
    CPC ....... *B25J 15/10* (2013.01); *A61F 2002/5001*
        (2013.01); *A61F 2002/5038* (2013.01); *A61F*
        *2002/5081* (2013.01); *A61F 2002/5089*
        (2013.01); *A61F 2002/5093* (2013.01); *A61F*
        *2002/543* (2013.01); *A61F 2002/587*
        (2013.01); *A61F 2002/701* (2013.01)

(58) Field of Classification Search
    USPC ........................................................ 294/213
    See application file for complete search history.

(56) References Cited

U.S. PATENT DOCUMENTS

| | | | | |
|---|---|---|---|---|
| 8,919,842 | B2 * | 12/2014 | Ihrke ................... | B25J 15/0009 |
| | | | | 901/29 |
| 9,120,220 | B2 * | 9/2015 | Bergelin .............. | A61H 1/0288 |
| 10,286,561 | B2 | 5/2019 | Miyazaki et al. | |
| 12,090,635 | B2 * | 9/2024 | Kim ...................... | B25J 15/0009 |
| 12,090,636 | B2 * | 9/2024 | Seki ....................... | B25J 9/1075 |
| 12,141,365 | B1 * | 11/2024 | Samulak ................. | G06F 3/017 |

| | | | | |
|---|---|---|---|---|
| 2007/0035143 | A1 | 2/2007 | Blackwell et al. | |
| 2010/0176615 | A1 * | 7/2010 | Okuda .................... | A61F 2/583 |
| | | | | 901/31 |
| 2011/0068595 | A1 | 3/2011 | Ihrke et al. | |
| 2011/0257765 | A1 * | 10/2011 | Evans ..................... | A61F 2/581 |
| | | | | 623/24 |
| 2012/0068486 | A1 * | 3/2012 | Kim ......................... | B25J 15/10 |
| | | | | 294/213 |
| 2013/0331949 | A1 | 12/2013 | Dehoff et al. | |
| 2018/0207005 | A1 * | 7/2018 | Chen ......................... | A61F 2/72 |
| 2020/0206950 | A1 * | 7/2020 | Fukaya ............... | B25J 15/0226 |

FOREIGN PATENT DOCUMENTS

| | | |
|---|---|---|
| CN | 108161958 A | 6/2018 |
| CN | 108555914 A | 9/2018 |
| CN | 108621144 A | 10/2018 |
| CN | 109591041 A | 4/2019 |
| CN | 110842962 A | 2/2020 |
| JP | 2006281380 A | 10/2006 |
| WO | 2009016478 A2 | 2/2009 |
| WO | 2017038836 A1 | 3/2017 |

OTHER PUBLICATIONS

Translation of International Search Report for International Application No. PCT/CN2020/133435; Date of Completion: Feb. 5, 2021; Date of Mailing: Mar. 3, 2021; 3 Pages.

Translation of Written Opinion for International Application No. PCT/CN2020/133435; Date of Completion: Feb. 22, 2021; Date of Mailing: Mar. 3, 2021; 5 Pages.

Written Opinion for International Application No. PCT/CN2020/133435; Date of Completion: Feb. 22, 2021; Date of Mailing: Mar. 3, 2021; 4 Pages.

* cited by examiner

DEXTEROUS HAND

CROSS-REFERENCE TO RELATED APPLICATION

This application is a continuation-in-part application of PCT International Application No. PCT/CN2020/133435 filed on Dec. 2, 2020, which claims the priority to and benefits of Chinese Patent Application No. 201911214168.1 filed on Dec. 2, 2019. The entire contents of the above applications are incorporated herein by reference for all purposes.

FIELD

This application belongs to the technical field of bionic dexterous hand, in particular relates to a 32-degree-of-freedom bionic flexible endoskeletal dexterous hand.

BACKGROUND

The bionic dexterous hand refers to a manipulator whose number of fingers, degrees of freedom, shape, and function are close to those of a human hand. It can operate objects flexibly and finely. It is suitable as a high-performance prosthesis or used in flexible assembly and other industrial scenarios. It can also replace personnel to work in hazardous environments such as pollution, positioning and radiation. It can be used by service robots with high versatility, and are key components of bionic or humanoid robots. The bionic dexterous hand is characterized by the small hand size and the large number of joints, which requires the transmission of large forces in a small space, and often requires that each joint can be independently controlled to achieve higher flexibility.

At present, most dexterous hands are driven by tendon, gear or hinged linkage. Among them, tendon transmission has the characteristics of being flexible and capable of transferring large force to hip joints, and is widely used in dexterous hand systems with a high number of degrees of freedom. In this method, the force and motion of the actuator located in the arm are transferred to the hand joint through the tendon (using steel wire or flexible rope), which can effectively balance the contradiction between the size constraint of the hand and the need to transfer large forces. In some schemes, a tendon sheath (i.e., a hose) is used to cover the tendon, so that the tendon can slide axially within the tendon sheath to restrain the direction of the tendon and provide protection. However, such method needs to pass a large number of tendons and tendon sheaths through the wrist, and the hands and wrists are not easy to disassemble/assemble and detach from/combine with the arms, thus is not easy to maintain. Therefore, a flexible way of disconnecting tendons and tendon sheaths, as well as disassembling hands and wrists and separating or combining them with arms, is needed for production, assemble/disassemble and maintenance.

Human joints are driven by a pair of muscle groups in an antagonistic manner. That is, when one group of muscles is tightened and the other group of muscles is released, the corresponding joint turns in one direction, and vice versa. The dexterous hand using tendon transmission can also simulate this method, so that each joint is driven antagonistically by a pair of actuators, that is, when the joint needs to be rotated in one direction, one of the actuators pulls the tendon, and the other actuator releases the tendon, and vice versa. In this way, joint stiffness can be controlled, which in turn allows for smooth operation and anti-interference robustness. However, this method requires a large number of motors, and how to effectively use the space of the forearm to arrange the actuator and transmission system is a difficult problem.

Some joints in human hand have two or more degrees of freedom (such as metacarpophalangeal joints and wrist joints), and the axes of these degrees of freedom are nearly orthogonal. Each degree of freedom is driven by different muscle groups, which can move flexibly and independently. The design of bionic dexterous hand joints should also make the axis of each degree of freedom of the corresponding joints as orthogonal as possible, so that the motion form is closest to the human hand, and the degrees of freedom of the joints are decoupled from each other, which is convenient for the calculation of control and motion planning. At present, many dexterous hand designs do not achieve the above goals, which brings certain difficulties to the calculation of control and motion planning.

Some joints in the human hand have passive degrees of freedom. For example, the metacarpophalangeal joint allows the finger to rotate slightly along the axis of the finger's proximal phalange under the impact of external force (i.e., circumduction), so that the finger can automatically and smoothly adapt to complex curved surfaces. It is of great significance for grasping and manipulating objects with complex shapes, such as holding a pen to write, using chopsticks, etc. The fingers need to circumduct slightly to match the shape of the pen or chopsticks. However, the current dexterous hands have not adopted these passive degrees of freedom, and the adaptability to the complex shaped objects is not good enough.

Human hands also have the ability to perform the opposition movement. The opposition movement refers to the movement where the tip of the thumb touches the tips of other fingers. It is a unique ability evolved in the long-term social production of human beings, enabling human hands to perform complex pinching actions and adapt the hand palm to objects with curved surfaces, such as grasping apples and light bulbs. For opposition movement, the thumb carpometacarpal joint shall have at least the DOF of flexion/extension, DOF of abduction/adduction, and DOF of circumduction, the thumb metacarpophalangeal joint shall have DOF of abduction/adduction, and the carpometacarpal joints of the ring finger and little finger shall have small ranges of DOF of flexion/extension and DOF of abduction/adduction (or simultaneously adopt DOF of circumduction). Most existing dexterous hands have not yet fully realized the opposition function, and it is difficult for them to perform complex pinching actions.

Most dexterous hands today adopt exoskeleton scheme, in which the shell is relatively rigid. The hand palm is usually a whole piece, and there is also insufficient space on the surface of the hand to be covered with a flexible bionic skin layer with a certain thickness, which is not conducive to performing compliant griping and manipulations.

SUMMARY

One of the purposes of this application is to provide a bionic flexible endoskeletal dexterous hand with 32 degrees of freedom, aiming to solve the following problems:

1. Existing dexterous hands need to make a large number of tendons and tendon sheaths pass through the wrist, so it is not easy to disassemble/assemble the hand and wrist freely and separate or combine with the arm, which is not easy to maintain.

2. The axes of various degrees of freedom in the existing dexterous hands are not orthogonal, which is not conducive to the calculation of control and motion planning.

3. The existing dexterous hands have not fully realized the opposition function, and each finger has no passive degrees of freedom, which makes it difficult to perform complex operations due to poor adaptability to objects with complex shapes.

4. Existing dexterous hands adopt exoskeleton scheme, which is not conducive to cover with bionic skin, and their shell is hard, which is not conducive to compliant operation.

In order to solve the above-mentioned problems, the technical scheme adopted in this application example is:

A 32-degree-of-freedom bionic endoskeletal dexterous hand, comprising a hand module; a wrist module; and a forearm module.

The hand module comprises a thumb unit; an index finger unit; a middle finger unit, a ring finger unit; a little finger unit, and a palm unit.

The thumb unit comprises a thumb distal phalange; a thumb proximal phalange; and a thumb distal joint.

The index finger unit comprises an index finger distal phalange; an index finger middle phalange; an index finger proximal phalange; an index finger distal joint; and an index finger proximal joint.

The middle finger unit comprises a middle finger distal phalange; a middle finger middle phalange; a middle finger proximal phalange; a middle finger distal joint; and a middle finger proximal joint.

The ring finger unit comprises a ring finger distal phalange; a ring finger middle phalange; a ring finger proximal phalange; a ring finger distal joint; and a ring finger proximal joint.

The little finger unit comprises a little finger distal phalange; a little finger middle phalange; a little finger proximal phalange; a little finger distal joint; and a little finger proximal joint.

The palm unit comprises a carpometacarpal base; a thumb metacarpal; an index finger metacarpal; a middle finger metacarpal; a ring finger metacarpal; a little finger metacarpal; a thumb carpometacarpal joint; a ring finger carpometacarpal joint; a little finger carpometacarpal joint; a ring finger metacarpal flexible constraint element; a little finger metacarpal flexible constraint element; a thumb metacarpophalangeal joint; an index finger metacarpophalangeal joint; a middle finger metacarpophalangeal joint; a ring finger metacarpophalangeal joint; and a little finger metacarpophalangeal joint.

The wrist module comprises a wrist joint and a wrist support frame.

The forearm module comprises a tendon sheath guide base and a actuator storage bin.

The thumb unit is hinged to the thumb metacarpal through the thumb metacarpophalangeal joint.

The index finger unit is hinged to the index finger metacarpal through the index finger metacarpophalangeal joint.

The middle finger unit is hinged to the middle finger metacarpal through the middle finger metacarpophalangeal joint.

The ring finger unit is hinged to the ring finger metacarpal through the ring finger metacarpophalangeal joint.

The little finger unit is hinged to the little finger metacarpal through the little finger metacarpophalangeal joint.

A palm-internal actuator is installed on each of the thumb metacarpal, the index finger metacarpal, the middle finger metacarpal, the ring finger metacarpal, and the little finger metacarpal.

The thumb metacarpal is hinged to the carpometacarpal base through the thumb carpometacarpal joint.

The index finger metacarpal is fixed to the carpometacarpal base.

The middle finger metacarpal is fixed to the carpometacarpal base.

The ring finger metacarpal is hinged to the carpometacarpal base through the ring finger carpometacarpal joint.

The little finger metacarpal is hinged to the carpometacarpal base through the little finger carpometacarpal joint.

The ring finger metacarpal flexible constraint element is configured to flexibly couple the middle finger metacarpal with the ring finger metacarpal.

The little finger metacarpal flexible constraint element is configured to flexibly couple the ring finger metacarpal with the little finger metacarpal.

The carpometacarpal base is hinged to the wrist support frame through the wrist joint.

The wrist support frame is fixed to the forearm module.

The tendon sheath guide base is installed at the junction of the wrist support frame and the forearm module.

A plurality of forearm-internal actuators are installed in the actuator storage bin.

An actuator driving circuit is installed in the actuator storage bin.

Each forearm-internal actuator's output shaft is equipped with a respective capstan.

The palm-internal actuator and the forearm-internal actuators are configured as rotary actuators.

The dexterous hand has 32 degrees of freedom. The thumb distal joint has DOF of flexion/extension. The thumb metacarpophalangeal joint has DOF of flexion/extension, DOF of abduction/adduction, and DOF of circumduction. The thumb carpometacarpal joint has DOF of circumduction, DOF of flexion/extension and DOF of abduction/adduction. The index finger distal joint has DOF of flexion/extension. The index finger proximal joint has DOF of flexion/extension. The index finger metacarpophalangeal joint has DOF of flexion/extension, DOF of abduction/adduction, and DOF of circumduction. The middle finger distal joint has DOF of flexion/extension. The middle finger proximal joint has DOF of flexion/extension. The middle finger metacarpophalangeal joint has DOF of flexion/extension, DOF of abduction/adduction, and DOF of circumduction. The ring finger distal joint has DOF of flexion/extension. The ring finger proximal joint has DOF of flexion/extension. The ring finger metacarpophalangeal joint has DOF of flexion/extension, DOF of abduction/adduction, and DOF of circumduction. The ring finger carpometacarpal joint has DOF of flexion/extension, and DOF of adduction/abduction. The little finger distal joint has DOF of flexion/extension, the little finger proximal joint has DOF of flexion/extension. The little finger metacarpophalangeal joint has DOF of flexion/extension, DOF of abduction/adduction, and DOF of circumduction. The little finger carpometacarpal joint has DOF of flexion/extension, and DOF of adduction/abduction. The wrist joint has DOF of flexion/extension and DOF of abduction/adduction.

Optionally, the axes of the DOF of flexion/extension, DOF of abduction/adduction, and DOF of circumduction of the thumb metacarpophalangeal joint are orthogonal, and the axes of the DOF of flexion/extension, DOF of abduction/adduction, and DOF of circumduction of the index finger metacarpophalangeal joint are orthogonal, and the axes of the DOF of flexion/extension, DOF of abduction/adduction, and DOF of circumduction of the middle finger metacarpophalangeal joint are orthogonal, and the axes of the DOF of flexion/extension, DOF of abduction/adduction, and DOF of circumduction of the ring finger joints are orthogonal, and the axes of the DOF of flexion/extension, DOF of abduction/adduction, and DOF of circumduction of the little finger metacarpophalangeal joint are orthogonal, and the axes of DOF of flexion/extension, and DOF of adduction/abduction of the ring finger carpometacarpal joint are orthogonal, and the axes of DOF of flexion/extension and DOF of adduction/abduction of the little finger carpometacarpal joint are orthogonal, and the axes of DOF of flexion/extension and DOF of abduction/adduction of the wrist joint are orthogonal to facilitate the calculation of control and motion planning.

DOF of circumduction of the thumb metacarpophalangeal joint, DOF of circumduction of the index finger metacarpophalangeal joint, DOF of circumduction of the middle finger metacarpophalangeal joint, DOF of circumduction of the ring finger metacarpophalangeal joint, DOF of circumduction of the little finger metacarpophalangeal joint, DOF of adduction/abduction of the ring finger carpometacarpal joint, and DOF of adduction/abduction of the little finger carpometacarpal joint are passive degrees of freedom driven by external forces.

The DOF of circumduction of the thumb metacarpophalangeal joint is driven by the palm-internal actuator installed within the thumb metacarpal through a first gear train.

The DOF of circumduction of the index finger metacarpophalangeal joint is driven by the palm-internal actuator installed within the index finger metacarpal through a second gear train.

The DOF of circumduction of the middle finger metacarpophalangeal joint is driven by the palm-internal actuator installed within the middle finger metacarpal through a third gear train.

The DOF of circumduction of the ring finger metacarpophalangeal joint is driven by the palm-internal actuator installed within the ring finger metacarpal through a fourth gear train.

The DOF of circumduction of the little finger metacarpophalangeal joint is driven by the palm-internal actuator installed within the little finger metacarpal through a fifth gear train.

DOF of flexion/extension of the thumb distal joint, DOF of flexion/extension of the thumb metacarpophalangeal joint, DOF of flexion/extension, DOF of abduction/adduction, and DOF of circumduction of the thumb carpometacarpal joint, DOF of flexion/extension of the index finger distal joint, DOF of flexion/extension of the index finger proximal joint, DOF of flexion/extension of the index finger metacarpophalangeal joint, DOF of flexion/extension of the middle finger distal joint, DOF of flexion/extension of the middle finger proximal joint, DOF of flexion/extension of the middle finger metacarpophalangeal joint, DOF of flexion/extension of the ring finger distal joint, DOF of flexion/extension of the ring finger proximal joint, DOF of flexion/extension of the ring finger metacarpophalangeal joint, DOF of flexion/extension of the ring finger carpometacarpal joint, DOF of flexion/extension of the little finger distal joint, DOF of flexion/extension of the little finger proximal joint, DOF of flexion/extension of the little finger metacarpophalangeal joint, DOF of flexion/extension of the little finger carpometacarpal joint, and DOF of flexion/extension and DOF of abduction/adduction of the wrist joint each is respectively driven by an antagonistic drive mechanism comprising a pair of the forearm-internal actuators, and are decoupled from each other, the antagonistic drive mechanism adopts tendon transmission.

The dexterous hand's one or more tendons are covered with a plurality of tendon sheaths that protect and guide the tendon, the tendon sheaths comprise one to multiple layers from inside to outside.

The tendon sheath guide base comprises a plurality of tendon sheath mounting interfaces.

An end of each tendon sheath is fixed with a tendon driven joint's joint base, and the other end is fixed with the tendon sheath mounting interfaces of the tendon sheath guide base.

In the antagonistic drive mechanism, the rotational end of a controlled joint is fixedly connected to any point on the tendon through a tendon fixing element, and the controlled degree of freedom of the controlled joint is jointly driven by a first forearm-internal actuator and a second forearm-internal actuator, the first forearm-internal actuator is configured to pull an end of the tendon through a first corresponding capstan fixedly connected to the first forearm-internal actuator's output shaft, thereby pulling the rotational end of the controlled joint so that said rotational end has a movement trend in a direction of the controlled degree of freedom, the second forearm-internal actuator is configured to pull an opposite end of the tendon through a second corresponding capstan fixedly connected to the second forearm-internal actuator's output shaft, thereby pulling the rotational end of the controlled joint so that said rotational end has a movement trend towards the opposite direction of the controlled degree of freedom, thus the first forearm-internal actuator and the second forearm-internal actuator constitute an antagonistic drive.

Speed and output force of the first forearm-internal actuator and the second forearm-internal actuator that constitute the antagonistic drive are configured to control motion, torque, joint damping and joint stiffness of the controlled joint. This allows the dexterous hand to take into account the operational flexibility and anti-interference resistance.

Joint angle sensor is installed at each joint of the dexterous hand to measure the rotation angle and angular velocity of each degree of freedom. The angular velocity can be obtained by differentiating angle with respect to time.

Joint force and torque sensors are installed at all or part of the joints of the dexterous hand.

The dexterous hand's one or more tendons are provided with tendon tension sensors.

The dexterous hand's one or more capstans are equipped with torque sensors to measure the torque in the capstan acted by each forearm-internal actuator's output shaft.

The joint base of each joint, which uses the tendon transmission, of the dexterous hand has respective tendon sheath mounting interfaces.

The thumb distal phalange, the index finger distal phalange, the middle finger distal phalange, the ring finger distal phalange, the little finger distal phalange, the index finger middle phalange, the middle finger middle phalange, the ring finger middle phalange, the little finger middle phalange, the thumb proximal phalange, the index finger proximal phalange, the middle finger proximal phalange, and the ring finger proximal phalange and the little finger proximal phalange are configured with light alloy or light non-metallic material with electromagnetic shielding layers to shield internal circuits and improve the ability to resist electromagnetic interference.

The length ratio of the phalanges of the thumb unit, the index finger unit, the middle finger unit, the ring finger unit, and the little finger unit are configured to simulate human hands. The thumb distal phalange, the index finger distal phalange, the middle finger distal phalange, the ring finger distal phalange and the little finger distal phalange each is configured as a hollow structure, the hollow structure is with a tapered surface on an outer side wall and an open bottom surface, and the hollow structure is configured to accommodate the joint force and torque sensors as well as circuit and signal lines.

The index finger middle phalange, the middle finger middle phalange, the ring finger middle phalange and the little finger middle phalange each is configured as a hollow tube, and the hollow tube is configured to accommodate the joint force and torque sensors as well as circuit and signal lines.

The thumb proximal phalange, the index finger proximal phalange, the middle finger proximal phalange, the ring finger proximal phalange and the little finger proximal phalange each is configured as a hollow tube with lateral projection at the base, the lateral projection is configured to accommodate metacarpophalangeal joint rotation angle sensor, and the hollow tube is configured to accommodate a circumduction reset device, the joint force and torque sensors as well as the circuit and signal lines.

The thumb distal joint, the index finger distal joint, the middle finger distal joint, the ring finger distal joint, the little finger distal joint, the index finger proximal joint, the middle finger proximal joint, the ring finger proximal joint, the little finger proximal joint are respectively configured to use a 1-degree-of-freedom interphalangeal joint universal module.

The 1-degree-of-freedom interphalangeal joint universal module has DOF of flexion/extension, and comprises an interphalangeal joint base, an interphalangeal joint rotational end, an interphalangeal joint flexion/extension shaft, and interphalangeal joint flexion/extension angle sensor.

The interphalangeal joint flexion/extension shaft has one or more first interfaces adapted to the interphalangeal joint flexion/extension angle sensor and one or more second interfaces to fix with the interphalangeal joint rotational end.

The interphalangeal joint base and the interphalangeal joint rotational end each has a respective mounting interface for mounting the phalanges or the joint force and torque sensors.

Installation method of the interphalangeal joint base comprises any one of:
directly connecting the interphalangeal joint base to the phalanges; and
firstly fixedly connecting the interphalangeal joint base to the joint force and torque sensor, and then fixing the joint force and torque sensor to the phalanges (This method is used to measure one to multi-dimensional force and torque of the 1-degree-of-freedom interphalangeal joint universal module.).

Installation method of the interphalangeal joint rotational end comprises any one of:
directly connecting the interphalangeal joint rotational end to the phalanges; and
firstly fixedly connecting the interphalangeal joint rotational end to the joint force and torque sensor, and then fixing the joint force and torque sensor to the phalanges (This method is used to measure one to multi-dimensional force and torque of the 1-degree-of-freedom interphalangeal joint universal module).

The carpometacarpal base has an installation interface to connect with the wrist joint, the thumb carpometacarpal joint, the ring finger carpometacarpal joint, the little finger carpometacarpal joint, the index finger metacarpal and the middle finger metacarpal, and is configured as the main force bearing component of the palm unit.

Main axes of the index finger metacarpal and the middle finger metacarpal are configured to form an included angle between 0 to 15 degrees, simulating a curved surface of a human hand palm.

The root of the ring finger metacarpal and the ring finger carpometacarpal joint form a evolute pair with DOF of adduction/abduction.

The root of the little finger phalange and the little finger carpometacarpal joint form a evolute pair with DOF of adduction/abduction.

The root of the thumb metacarpal is configured with the thumb carpometacarpal joint to form a first evolute pair with DOF of flexion/extension and DOF of abduction/adduction, and is fixed with a V-shape groove pulley used for the tendon transmission.

The DOF of flexion/extension and abduction/adduction of the thumb carpometacarpal joint has 1-degree-of-freedom, which couples the flexion/extension movements with abduction/adduction movements, the axis of the DOF of flexion/extension and abduction/adduction of the thumb carpometacarpal joint and the axis of the DOF of abduction/adduction of the thumb metacarpophalangeal joint are configured to form an included angle of 30 to 60 degrees, simulating the motion pattern of simultaneous flexion/extension and abduction/adduction of the thumb carpometacarpal joint when the hand is doing an opposition movement, so as to realize a opposition function.

The thumb carpometacarpal joint comprises a thumb carpometacarpal joint base, a thumb carpometacarpal joint rotational end, thumb carpometacarpal joint circumduction angle sensor, and thumb carpometacarpal joint flexion/extension and abduction/adduction angle sensor.

An end of the thumb carpometacarpal joint rotational end and the thumb carpometacarpal joint base form a revolute pair with DOF of circumduction, and is coaxially fixed with a V-shape groove pulley used for tendon transmission. An opposite end of the thumb carpometacarpal rotational end and the thumb metacarpal form a second evolute pair with DOF of flexion/extension and abduction/adduction.

The thumb carpometacarpal rotational end includes the tendon sheath mounting interfaces.

The ring finger metacarpal flexible constraint element is configured to restrain movement range of the ring finger metacarpal, and to keep the ring finger metacarpal in resting position when there is no external force, when the ring finger metacarpal is performing flexion movement, the ring finger metacarpal flexible constraint element holds the ring finger metacarpal and adduction motion occurs incidentally.

The little finger metacarpal flexible constraint element is configured to restrain movement range of the little finger metacarpal, and to keep the little finger metacarpal in resting position when there is no external force, when the little finger metacarpal is performing flexion movement, the little finger metacarpal flexible constraint element holds the little finger metacarpal and the adduction motion occurs incidentally.

When the palm unit is subjected to external forces from little finger side to thumb side (such as during a handshake), the adduction motion of the ring finger metacarpal and the little finger metacarpal can occur simultaneously, and the ring finger metacarpal flexible constraint element and the ring finger metacarpal flexible constraint element absorbs and cushions said external forces.

The ring finger carpometacarpal joint comprises a ring finger carpometacarpal joint base, a ring finger carpometacarpal rotational end, ring finger carpometacarpal joint flexion/extension angle sensor, and ring finger carpometacarpal joint limiting pin, ring finger carpometacarpal joint adduction/abduction angle sensor.

The little finger carpometacarpal joint comprises a little finger carpometacarpal joint base, a little finger carpometacarpal rotational end, little finger carpometacarpal joint flexion/extension angle sensor, and little finger carpometacarpal joint limiting pin, little finger carpometacarpal joint adduction/abduction angle sensor.

The thumb metacarpophalangeal joint, the index finger metacarpophalangeal joint, the middle finger metacarpophalangeal joint, the ring finger metacarpophalangeal joint, the little finger metacarpophalangeal joint are respectively configured to use a 3-degree-of-freedom metacarpophalangeal joint universal module.

The 3-degree-of-freedom metacarpophalangeal joint universal module has DOF of flexion/extension, DOF of abduction/adduction, and DOF of circumduction, the axes of said DOF of flexion/extension, DOF of abduction/adduction, and DOF of circumduction are orthogonal to facilitate calculation of control and motion planning.

The 3-degree-of-freedom metacarpophalangeal joint universal module comprises a metacarpophalangeal joint abduction/adduction rotational end, a metacarpophalangeal joint abduction/adduction shaft, a metacarpophalangeal joint flexion/extension rotational end, a metacarpophalangeal joint flexion/extension shaft, a circumduction reset device, metacarpophalangeal joint flexion/extension angle sensor, metacarpophalangeal joint abduction/adduction angle sensor, metacarpophalangeal joint circumduction angle sensor, and a metacarpophalangeal joint tendon guide groove.

The cylindrical surface of the metacarpophalangeal joint abduction/adduction shaft has a gap to fix with and fit the metacarpophalangeal joint flexion/extension shaft, and an end thereof has a first interface adapted to the metacarpophalangeal joint abduction/adduction angle sensor.

The cylindrical surface of the metacarpophalangeal joint flexion/extension shaft has a gap to fix with and fit the metacarpophalangeal joint abduction/adduction shaft, and an end thereof has a second interface adapted to the metacarpophalangeal joint flexion/extension angle sensor.

The metacarpophalangeal joint flexion/extension rotational end comprises a rotational joint base that supports the distal phalanges to perform circumduction motion and bears force.

The circumduction reset device is installed at the circumduction joint base of the metacarpophalangeal joint flexion-extension rotational end, and comprises an elastic reset element (such as a reset spring), so that the finger units perform the rotational motion when subjected to external torsion, and the amplitude of the circumduction motion is positively related to said external torsion, and when the external torsion disappears, the finger units returns to original position thereof.

The circumduction reset device has a third interface for installing a strain gauge or the joint force and torque sensor, so as to measure one to multi-dimensional forces and torques of the 3-degree-of-freedom metacarpophalangeal joint universal module. The metacarpophalangeal joint tendon guide groove is fixedly connected to the metacarpophalangeal joint abduction/adduction rotational end, and tendon and the tendon sheaths passing the metacarpophalangeal joint adhere to the metacarpophalangeal joint tendon guide groove to slide, the metacarpophalangeal joint tendon guide groove is configured to guide the direction of the tendon and tendon sheaths so as to reduce the interference of the metacarpophalangeal joint on the tendon that drives the DOF of flexion/extension of the metacarpophalangeal joint, and the interference of the metacarpophalangeal joint on the tendon sheath that spans the 3-degree-of-freedom metacarpophalangeal joint universal module, the lateral section of the metacarpophalangeal joint tendon guide groove is semicircular, the tendon maintains a constant length of transmissional arm of force during transmission (which is equal to the radius of the metacarpophalangeal joint tendon guide groove).

A respective palm-internal actuator installed on any one of the thumb metacarpal, the index finger metacarpal, the middle finger metacarpal, the ring finger metacarpal, and the little finger metacarpal is configured to drive the respective metacarpophalangeal joint abduction/adduction rotational end hinged to respective metacarpal through the respective gear train to perform abduction/adduction motion.

The axis of the wrist joint's DOF of abduction/adduction and the axis of the wrist joint's DOF of flexion/extension are orthogonal.

The wrist joint comprises a wrist joint abduction/adduction rotational end, a wrist joint abduction/adduction shaft, a wrist joint flexion/extension rotational end, a wrist joint flexion/extension shaft, wrist joint abduction/adduction angle sensor, wrist joint flexion/extension angle sensor and a wrist joint tendon guide groove.

An end of the wrist joint abduction/adduction shaft is provided with a coaxial driven V-shape groove pulley, a middle part of the wrist joint abduction/adduction shaft has a gap for locking and matching with the wrist joint flexion/extension shaft, and an opposite end of the wrist joint abduction/adduction shaft comprises a first interface adapted to the wrist joint abduction/adduction angle sensor.

The cylindrical surface of the wrist joint flexion/extension shaft has a gap that is tightly matched with the wrist joint abduction/adduction shaft, and an end thereof comprises a second interface adapted to the wrist joint flexion/extension angle sensor.

The wrist joint flexion/extension rotational end comprises a third interface to connect with the carpometacarpal base, and a fourth interface for installing the joint force and torque sensor (to measure one to multi-dimensional forces and torques of the wrist).

The wrist joint tendon guide groove is fixedly connected to the wrist joint abduction/adduction rotational end, and the tendon driving the wrist joint's DOF of flexion/extension adheres to the wrist joint tendon guide groove to slide, so as to attenuate the interference to the tendons that drive the DOF of flexion/extension of the wrist joint during the abduction/adduction motion of the wrist joint, the side section of the wrist joint tendon guide groove is semi-circular, and the tendon maintains a constant length of transmissional arm of force during transmission (which is equal to the radius of the wrist joint tendon guide groove).

The wrist support frame comprises the tendon sheath mounting interfaces, a wrist joint base, and a forearm mounting base, used for coupling the wrist joint and the forearm module together.

An improved solution is that each palm-internal actuator is configured to use linear actuators, and to drive a respective metacarpophalangeal joint abduction/adduction rotational end through a hinged linkage mechanism to perform abduction/adduction motion.

An improved solution is that each forearm-internal actuator is configured to use linear actuators, and each forearm-internal actuator's output shaft is fixedly connected to the tendon. Another improved solution is that each forearm-internal actuator is configured to use rotary actuators, and each forearm-internal actuator's output shaft is not fixedly connected to the tendon, instead, a lead screw mechanism is used to convert the rotary motion of each forearm-internal actuator's output shaft into a linear motion. Each forearm-internal actuator's output shaft is fixedly connected to the screw mechanism's lead screw, and the lead screw mechanism's linear moveable end of is fixed to the tendon.

If the forearm-internal actuators each adopts a rotary actuator, a servo, a DC motor or a brushless motor can be used. If the inner actuator of the forearm adopts a linear actuator, artificial muscles or linear motors can be used.

The forearm-internal actuators are divided into the main joint actuators, auxiliary joint actuators, and wrist joint actuators according to the magnitude of the peak output force or peak output torque and the driving object. In terms of the magnitude of the peak output force or peak output torque, the main joint actuators' is the smallest, the auxiliary joint actuators' is in the middle, and the wrist joint actuators' is the largest.

The main joint actuators are used to drive the DOF of flexion/extension of the thumb distal joint, the DOF of flexion/extension of the thumb metacarpophalangeal joint, the DOF of flexion/extension of the thumb carpometacarpal joint, the DOF of flexion/extension of the index finger distal joint, the DOF of flexion/extension of the index finger proximal joint, the DOF of flexion/extension of the index finger metacarpophalangeal joint, the DOF of flexion/extension of the middle finger distal joint, the DOF of flexion/extension of the middle finger proximal joint, the DOF of flexion/extension of the middle finger metacarpophalangeal joint, the DOF of flexion/extension of the ring finger distal joint, the DOF of flexion/extension of the ring finger proximal joint, the DOF of flexion/extension of the ring finger metacarpophalangeal joint, the DOF of flexion/extension of the little finger distal joint, the DOF of flexion/extension of the little finger proximal joint, and the DOF of flexion/extension of the little finger metacarpophalangeal joint.

The auxiliary joint actuators are used to drive the DOF of circumduction of the thumb carpometacarpal joint, the DOF of flexion/extension of the ring finger carpometacarpal joint, and the DOF of flexion/extension of the little finger carpometacarpal joint.

The wrist joint actuators are used to drive the DOF of flexion/extension and the DOF of abduction/adduction of the wrist joint.

The layout of some or all of the forearm-internal actuators in the forearm module includes one or more of:

installing some or all of the forearm-internal actuators in multiple rows from the thumb side to the little finger side; and/or installing some or all of the forearm-internal actuators in multiple rows from the hand side to the elbow side; and/or dividing some or all of the forearm-internal actuators into a plurality of pairs, each pair is configured to drive a respective degree of freedom to form the antagonistic drive, a mounting method for each pair comprises:

installing the respective forearm-internal actuators of each pair in the opposite direction, the respective forearm-internal actuators comprise a respective first forearm-internal actuator and a respective second forearm-internal actuator, the respective first forearm-internal actuator's output shaft is facing hand back side and the respective second forearm-internal actuator's output shaft is facing hand palm side; or installing the respective forearm-internal actuators of each pair in the opposite direction, the respective first forearm-internal actuator's output shaft is facing the thumb side of the hand and the respective second forearm-internal actuator's output shaft is facing the little finger side; or installing the respective forearm-internal actuators of each pair in the same direction, with the respective forearm-internal actuators' output shaft facing the hand back side; or installing the respective forearm-internal actuators of each pair in the same direction, with the respective forearm-internal actuators' output shaft facing the hand palm side; or installing the respective forearm-internal actuators of each pair in the same direction, with the respective forearm-internal actuators' output shaft facing the thumb side; or installing the respective forearm-internal actuators of each pair in the same direction, with the respective forearm-internal actuators' output shaft facing the little finger side.

Preferably, in order to make full use of the space in the forearm module, some or all of the forearm-internal actuators in the forearm module adopt the following layout:

1) The wrist joint actuator is placed in the actuator storage bin closest to the wrist joint. A set of wrist joint actuators that drive the DOF of abduction/adduction of the wrist joints are installed in the same direction. The output shaft is facing the hand back side. A set of wrist joint actuators that drive the wrist joint's DOF of flexion/extension are installed facing each other, with the output shaft facing the hand back side and hand palm side, respectively.

2) The main joint actuators are placed in the actuator storage bin away from the wrist joint. The main joint actuators of each group are installed facing each other, and is divided into the main joint actuators facing the hand palm side and the main joint actuators facing the hand back side, that is, the output shaft of main joint actuators facing the hand palm side faces the palm side of the hand, while the output shaft of main joint actuators facing the hand back side faces the back side of the hand.

3) The auxiliary joint actuators are placed between the wrist joint actuator and the main joint actuator. The auxiliary joint actuators of each group are installed facing each other, and the output shaft faces the hand back side and the hand palm respectively.

4) The main joint actuators are arranged in 5 columns from the thumb side to the little finger side, and each column corresponds to a finger unit, that is, starting from the thumb side, the first column corresponds to the thumb unit, the second column corresponds to the index finger unit, the third column corresponds to the middle finger unit, the fourth column corresponds to the ring finger unit, and the fifth column corresponds to the little finger unit.

Each column of the main joint actuators is arranged in three groups from the hand side to the elbow side (there are a total of 6 rows). Each group includes a pair of the main joint actuators that collectively drive 1 degree of freedom of the corresponding finger unit in the column. That is, starting from the hand side, the first group of column 1 drives the DOF of flexion/extension and DOF of abduction/adduction of the thumb carpometacarpal joint, the second group of column 1 drives the DOF of flexion/extension of the thumb metacarpophalangeal joint, and the third group of column 1 drives the DOF of flexion/extension of the thumb distal joint. The first group of column 2 drives the DOF of flexion/extension of the index finger metacarpophalangeal joint, the second group of column 2 drives the DOF of flexion/extension of the index finger proximal joint, the third group of column 3 drives the DOF of flexion/extension of the index finger distal joint. The first group of column 3 drives the DOF of flexion/extension of the middle finger metacarpophalangeal joint, the second group of column 3 drives the DOF of flexion/extension of the middle finger proximal joint, and the third group of column 3 drives the DOF of flexion/extension of the middle finger distal joint. The first group of column 4 drives the DOF of flexion/extension of the ring finger metacarpophalangeal joint, the second group of column 4 drives the DOF of flexion/extension of the ring finger proximal joint, and the third group of column 4 drives the DOF of flexion/extension of the ring finger distal joint. The first group of column 5 drives the DOF of flexion/extension of the little finger metacarpophalangeal joint, the second group of column 5 drives the DOF of flexion/extension of the little finger proximal joint, and the third group of column 5 drives the DOF of flexion/extension of the little finger distal joint.

The forearm module's capstans respectively has one or more diameters, and each of the forearm module's capstans is respectively distributed on the forearm module's hand back side, forearm module's hand palm side, forearm module's thumb side, or the forearm module's little finger side, and some or all of the capstans on each side are divided into one to multiple layers.

Preferably, in order to make full use of the space in the forearm module, a large number of capstans are integrated into the compact forearm module to provide suitable motion range for each joint, and to avoid the large number of capstans and tendons to interfere with each other. Some or all of the capstans in the forearm module has the following layout:

1) Four kinds of capstans with different diameters are used. They are divided into type I capstan, type II capstan, type III capstan and type IV capstan according to the diameter of the capstan.

2) The DOF of flexion/extension of the thumb distal joint, DOF of flexion/extension of the index finger distal joint, DOF of flexion/extension of the middle finger distal joint, DOF of flexion/extension of the ring finger distal joint, and DOF of flexion/extension of the little finger distal joint are configured to be driven by said type IV capstan.

3) The DOF of flexion/extension of the thumb metacarpophalangeal joint, the DOF of flexion/extension of the index finger proximal joint, the DOF of flexion/extension of the middle finger proximal joint, the DOF of flexion/extension of the ring finger proximal joint, and the DOF of flexion/extension of the little finger distal joint are configured to be driven by said type III capstan.

4) The flexion, extension and DOF of abduction/adduction of the thumb carpometacarpal joint, the DOF of flexion/extension of the index finger metacarpophalangeal joint, the DOF of flexion/extension of the middle finger metacarpophalangeal joint, the DOF of flexion/extension of the ring finger metacarpophalangeal joint, and the DOF of flexion/extension of the little finger metacarpophalangeal joint are configured to be driven by said type II capstan.

5) The DOF of circumduction of the thumb carpometacarpal joint, the DOF of flexion/extension of the ring finger carpometacarpal joint, the DOF of flexion/extension of the wrists of the little finger carpometacarpal joint, and the DOF of flexion/extension of the wrist joint and the DOF of abduction/adduction are configured to be driven by said type I capstan.

6) The capstans of the main joint actuators facing the hand palm side on column 1, column 3, column 5 are installed on the inner layer of the hand palm side of the forearm module. The capstans of the main joint actuators facing hand palm side on column 2 and column 4 are installed on the outer layer of the hand palm side of the forearm module.

7) The capstans of the main joint actuators facing the hand back side on column 1, column 3, column 5 are installed on the outer layer of the hand back side of the forearm module. The capstans of the main joint actuators facing hand palm side on column 2 and column 4 are installed on the inner layer of the hand back side of the forearm module.

The actuator storage bin comprises one or more sub storage bins, if the number of the sub storage bins is more than one, sub storage bins can be disassembled or assembled with each other, which is convenient for each sub storage bin to be independently assembled, debugged, and maintained.

The plurality of tendon sheath mounting interfaces of the tendon sheath guide base are respectively distributed on the back side and the palm side of the tendon sheath guide base, the plurality of tendon sheath mounting interfaces on each side are arranged in one to multiple layers, so that multiple tendons and tendon sheaths can smoothly cross the wrist module to each joint of the hand module, reducing mutual interference, and the tendon sheath guide base has a first interface adapted to the wrist support frame and a second interface adapted to the forearm module.

The one or more tendon sheaths of the dexterous hand are respectively mounted at one end of each tendon sheath by a detachable tendon sheath fixing element on the tendon sheath mounting interfaces of the tendon sheath guide base, and the one or more tendon sheaths of the dexterous hand are respectively mounted at the opposing end of each tendon sheath on the tendon sheath mounting interfaces of the joint base of the joints using tendon transmission through the detachable tendon sheath fixing element.

The tendon sheath fixing element enables the tendon sheath to be easily installed or removed from the tendon sheath guide base.

The tendon's part, which is between the capstan and the tendon sheath guide, is provided with a tendon coupling, the tendon coupling can be disconnected or coupled so that the tendon is disconnected or coupled from the middle of the tendon, and the maximum outer diameter of the tendon coupling is smaller than the inner diameter of each tendon sheath mounting interface of the tendon sheath guide base, so that the tendon coupling can pass through the tendon sheath mounting interface along with the tendon.

The dexterous hand uses the tendon sheath fixing element and tendon coupling, so that the hand module and the wrist module of the dexterous hand can be assembled with the forearm module or separated conveniently, which is convenient for production and maintenance.

The thumb distal joint, the thumb metacarpophalangeal joint, the index finger distal joint, the index finger proximal joint, the index finger metacarpophalangeal joint, the middle finger distal joint, the middle finger proximal joint, the middle finger metacarpophalangeal joint, the ring finger distal joint, the ring finger proximal joint, the ring finger metacarpophalangeal joint, the little finger distal joint, the little finger proximal joint, the little finger metacarpophalangeal joint each comprises a type I tendon sheath restraint element.

The wrist joint is equipped with a type II tendon sheath restraint element,

The thumb metacarpal, the index finger metacarpal, the middle finger metacarpal, the ring finger metacarpal, the little finger metacarpal each is equipped with a type III tendon sheath restraint element on the upper surface and the lower surface thereof.

A type IV tendon sheath restraint element is installed on each of the index finger proximal phalange's hand back side and hand palm side, the middle finger proximal phalange's hand back side and hand palm side, the ring finger proximal phalange's hand back side and hand palm side, the little finger proximal phalange's hand back side and hand palm side.

The type I tendon sheath restraint element is a first flexible element that can flex, and comprises one or more type I tendon sheath restraint element's guide grooves or first guide holes for guiding one to four of the tendon sheaths to slide along respective axes thereof.

The type II tendon sheath restraint element is a second flexible element that can flex, comprises one or more type II tendon sheath restraint element's guide grooves or guide holes for guiding at least five of the tendon sheaths to slide along respective axes thereof, and has a structure allowing one or more of the tendon sheaths that pass through the type II tendon sheath restraint element to curl respectively inside the type II tendon sheath restraint element.

The type III tendon sheath restraint element comprises one or more type III tendon sheath restraint element's guide grooves or guide holes for guiding one or more of the tendon sheaths to slide along respective axes thereof, and has a structure allowing one or more of the tendon sheaths that pass through the type III tendon sheath restraint element to curl respectively inside the type II tendon sheath restraint element.

The type IV tendon sheath restraint element comprises one or more type IV tendon sheath restraint element's guide grooves or guide holes for guiding one or more of the tendon sheaths to slide along respective axes thereof.

The dexterous hand is configured to adopt a tendon transmission layout comprising:

1) Distributing a plurality of the tendons on the dexterous hand's hand back side and hand palm side, an end of the plurality of the tendons is fixedly connected to a corresponding capstan, a starting end of the tendon sheath of the plurality of the tendons is fixed to the tendon sheath mounting interfaces on the tendon sheath guide base's hand back side and hand palm side through a tendon sheath fixing element, respectively, the plurality of the tendons are passing through said tendon sheath mounting interfaces and extend towards the wrist module.

2) The tendons, that drive the wrist joint, are configured to pass the wrist support framework's tendon sheath mounting interfaces through the tendon sheaths thereof, the tendons that drive the wrist joint are respectively connected to a wrist joint abduction/adduction rotational end and a wrist joint flexion/extension rotational end, the tail ends of the tendon sheaths thereof are fixedly connected to the wrist support framework's tendon sheath mounting interfaces through the tendon sheath fixing element.

3) Other tendons and the tendon sheaths thereof are configured to pass the wrist joint at the dexterous hand's hand back side and hand palm side respectively, and directions and curling spaces of said other tendons and of the tendon sheaths of said other tendons are restrained by large joint's tendon sheath flexible restraint elements installed at the wrist module, said other tendons and the tendon sheaths thereof are then configured to converge at the carpometacarpal base's hand back side and hand palm side.

4) Each tendon, that drives the thumb carpometacarpal joint's DOF of flexion/extension and abduction/adduction, the ring finger carpometacarpal joint's DOF of flexion/extension and the little finger carpometacarpal joint's DOF of flexion/extension, is configured to pass a corresponding carpometacarpal joint base's tendon sheath mounting interfaces through the tendon sheath thereof, and is connected to a corresponding carpometacarpal joint rotational end, a tail end of a respective tendon sheath thereof is fixedly connected to the corresponding carpometacarpal joint base's tendon sheath mounting interfaces through the tendon sheath fixing element.

5) T tendons, that drives the thumb carpometacarpal joint's DOF of circumduction, are fixedly connected to the thumb metacarpal's V-shape groove pulley, and the tail ends of the tendon sheaths thereof are fixedly connected to the thumb carpometacarpal joint rotational end's tendon sheath mounting interfaces through the tendon sheath fixing element.

6) Each tendon, that drives a respective finger unit and said respective finger unit's corresponding metacarpophalangeal joints, as well as the respective tendon sheath thereof are configured to pass through the respective finger unit's metacarpal's hand back side and hand palm side respectively, and are configured to be divided into two to three layers by the type III tendon sheath restraint element installed at the respective finger unit's metacarpal's hand back side and hand palm side so as to restrain respective direction and respective curling space of said each tendons and of the respective tendon sheath of said each tendon.

7) The tendons, that pass the thumb metacarpal, and the tendon sheaths thereof are divided into first inner layers and first outer layer on each side, the tendons on each side's first inner layers are configured to drive the thumb metacarpophalangeal joint's DOF of flexion/extension, and are fixedly connected to a thumb metacarpophalangeal joint flexion/extension rotational end, the tail ends of the tendon sheaths thereof are fixedly connected to the thumb metacarpal, the tendons on each side's first outer layers are configured to drive the thumb distal joint's DOF of flexion/extension, and are configured to continue to extend towards the thumb proximal phalange along with the tendon sheaths thereof, directions of said tendons and of tendon sheaths thereof are restrained by small joint's tendon sheath flexible restraint elements when said tendons and tendon sheaths thereof are passing the thumb metacarpophalangeal joint, said tendons are fixedly connected to the thumb distal joint's interphalangeal joint rotational end, the tail ends of the tendon sheaths thereof are fixedly connected to the thumb distal joint's interphalangeal joint base through the tendon sheath fixing element.

8) The tendons, that pass the index finger metacarpal, the middle finger metacarpal, the ring finger metacarpal, and the little finger metacarpal, and the tendon sheaths thereof are divided into second inner layers, second middle layers and second outer layer on each side, the tendons on each side's second inner layers are configured to drive the respective finger unit's finger metacarpophalangeal joints DOF of flexion/extension, and are fixedly connected to a metacarpophalangeal joint flexion/extension rotational end, and the tail ends of the tendon sheaths thereof are fixedly connected to corresponding finger metacarpal, the tendons on each side's second middle layers and second outer layers are configured to respectively drive the respective finger unit's proximal joints' DOF of flexion/extension and respective finger unit's distal joints' DOF of flexion/extension, and are configured to continue to extend towards the respective finger unit's proximal phalange along with the tendon sheaths thereof, said tendons' directions are restrained by the small joint's tendon sheath flexible restraint elements when said tendons are passing the respective finger unit's finger metacarpophalangeal joints, 9) The tendons, that drives the index finger unit's proximal joints' DOF of flexion/extension, the middle finger unit's proximal joints' DOF of flexion/extension, the ring finger unit's proximal joints' DOF of flexion/extension, and the little finger unit's proximal joints' flexion/extension, and the tendon sheaths thereof are configured to pass the respective finger unit's proximal phalange' hand back side and hand palm side, said tendons are fixedly connected to the respective finger unit's proximal joints' interphalangeal joint rotational end, the tail ends of the tendon sheaths thereof are fixedly connected to the respective finger unit's proximal joints' interphalangeal joint base through the tendon sheath fixing element.

10) When the tendons, that drive the index finger unit's distal joints' flexion/extension, the middle finger unit's distal joints' DOF of flexion/extension, the ring finger unit's distal joints' DOF of flexion/extension, and the little finger unit's distal joints' flexion/extension, and the tendon sheaths thereof are passing the respective finger unit's proximal phalanges, directions of said tendons and of the tendon sheaths thereof are restrained by the type IV tendon sheath restraint element fixed to the respective finger unit's proximal phalange' hand back side and hand palm side, said tendons and the tendon sheaths thereof are configured to slide along the axis of the type IV tendon sheath restraint element, when said tendons and the tendon sheaths thereof are passing the respective finger unit's proximal joint, directions of said tendons and of the tendon sheaths thereof are restrained by the small joint's tendon sheath restraint element, said tendons are fixedly connected to the respective finger unit's distal joints' interphalangeal joint rotational end, the tail ends of the tendon sheaths thereof are fixedly connected to the respective finger unit's distal joints' interphalangeal joint base through the tendon sheath fixing element.

Axis position of each DOF of each joint of the dexterous hand mimics that of the human hand, and the dexterous hand's movement form is close to the human hand, and can be well suited for operations that the human hand can perform.

The structure of the hand module is endoskeletal, with sufficient space on the outer surface.

The dexterous hand is covered by a bionic skin, a flexible jacket, or a rigid shell with a certain thickness, which is used to protect the internal structure and make the dexterous hand suitable for grasping and automatically adapting to complex curved objects.

The rigid shell is configured to cover the dexterous hand in segments according to the phalanges of each finger unit, the palm unit, the wrist module, and the forearm module, The bionic skin or the flexible jacket is configured to cover the dexterous hand as a whole, or cover in accordance with the whole of each finger unit or each phalange of the finger unit, the palm unit, the wrist module, and the forearm module in sections.

The bionic skin, the flexible jacket, the rigid shell adopts materials that are waterproof and dustproof and chemical erosion prevention, and each comprises an electromagnetic shielding layer, and/or a protective layer that shields or attenuates ionizing radiation.

The beneficial effects of the present invention are as follows. The proposed 32-degree-of-freedom bionic endoskeletal dexterous hand draws insights from the anatomical structure of a human hand. The structure of the hand module is endoskeletal, and there is enough space on the outside to cover the flexible bionic skin with a certain thickness, providing the basis for tactile perception, compliant operation and touch. The joints adopt dual-actuator antagonistic drive, which can control joint damping and joint stiffness, taking into account the operational flexibility and anti-interference robustness. The tendon joints and tendon sheath fixing elements are used. The tendons and tendon sheaths are easy to be connected or removed, so that the hand and wrist are easy to be assembled or separated from the forearm, which is convenient for production and maintenance. The metacarpophalangeal joints of the five fingers have DOF of circumduction, allowing the fingers to automatically and smoothly adapt to objects with complex curved surfaces (such as holding a pen, using chopsticks, etc.). The thumb carpometacarpal joint has two degrees of freedom such as DOF of flexion/extension and abduction/adduction, and DOF of circumduction. The thumb metacarpophalangeal joint has DOF of abduction/adduction, and the ring finger carpometacarpal joint and little finger carpometa-carpal joint have DOF of flexion/extension and DOF of adduction/abduction, and can perform opposition movements to perform complex pinch operations and adapt the hand palm to those operated objects with complex surfaces (such as holding apples, bulbs, etc.). The axes of each DOF of any multi-degree-of-freedom joint are orthogonal to each other, which is beneficial to calculation of control and motion planning. The layout of the actuator, capstan, tendon and tendon sheath can make full use of the tight space of the dexterous hand, so that the overall size of the dexterous hand is consistent with the human hand. The dexterous hand is very suitable for the smooth operation of complex shaped objects, easy to produce, disassemble and maintain, and is very suitable for high-end prosthetics or as a high-performance versatile robot dexterous hand or end-effector device. The dexterous hand can be equipped with flexible or rigid shell, flexible jacket or bionic skin that can be waterproof, dustproof and prevent chemical erosion, and can shield or weaken ionizing radiation. It can replace personnel to work in dangerous environment with pollution, contamination and radiation.

BRIEF DESCRIPTION OF DRAWINGS

In order to describe the embodiments of the present disclosure more clearly, a brief introduction regarding the accompanying drawings that need to be used for describing the embodiments of the present disclosure or demonstrated technology is given below. It is apparent that the accompanying drawings described below are only some embodiments of the present disclosure, the person of ordinary skill in the art may also obtain other drawings according to these drawings without paying creative effort.

DETAILED DESCRIPTION OF EMBODIMENTS

In the following, the technical solutions in the embodiments of the present invention will be clearly and completely described with reference to the drawings in the embodiments of the present invention. Obviously, the described embodiments are only a part of the embodiments of the present invention, but not all of the embodiments.

In order to explain the technical scheme of this application, the following details are given in combination with the attached drawings and embodiments.

Figure 1:
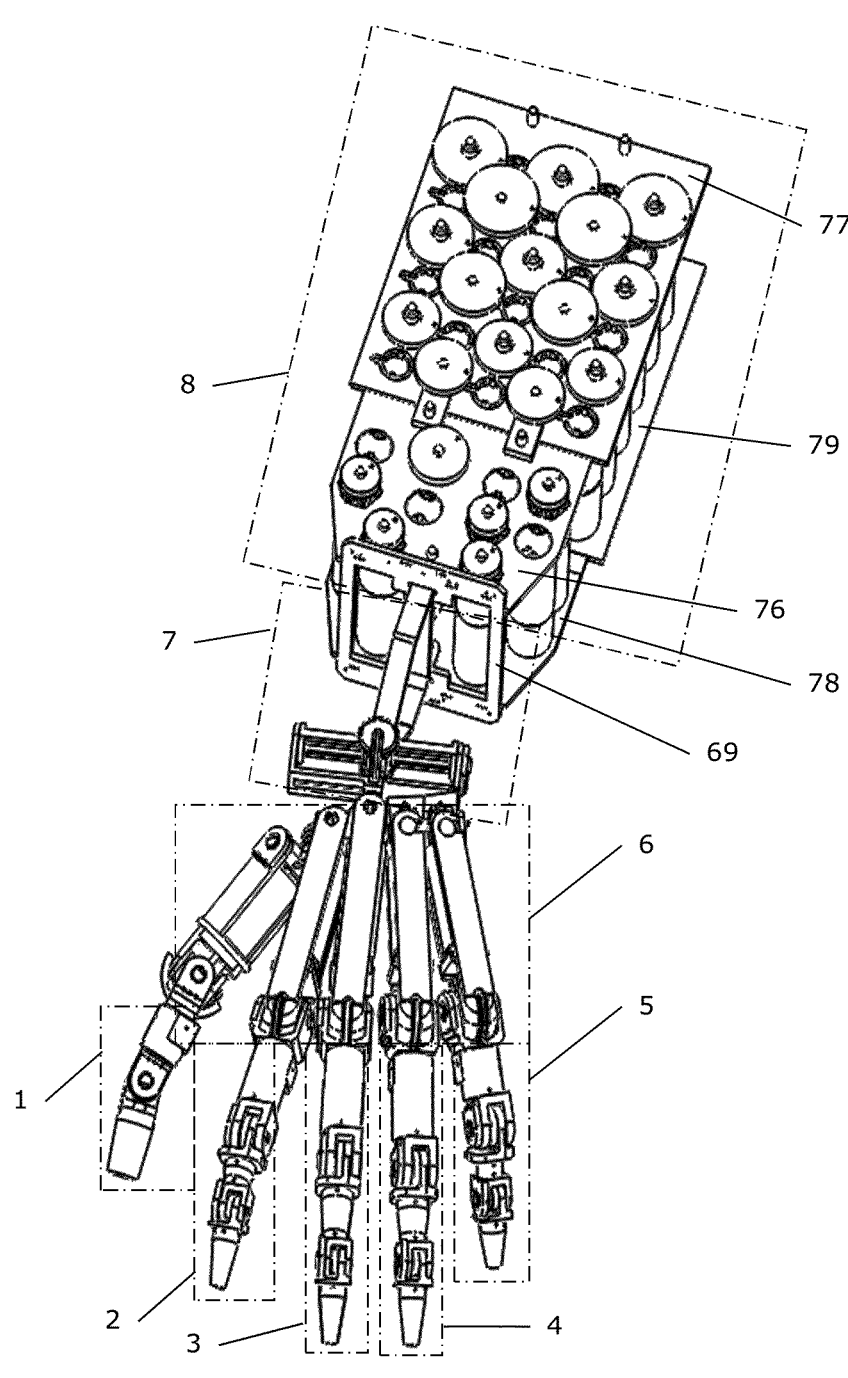
FIG. 1 is a schematic diagram of the overall structure of a 32-degree-of-freedom bionic flexible endoskeletal dexterous hand provided by this application.
Figure 2:
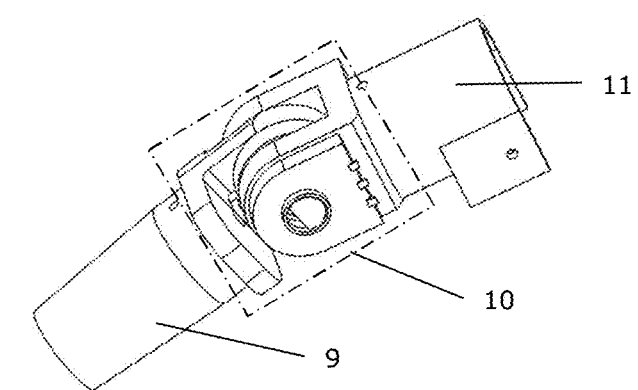
FIG. 2 is a schematic diagram of a thumb unit of a 32-degree-of-freedom bionic flexible endoskeletal dexterous hand provided by this application.
Figure 3:
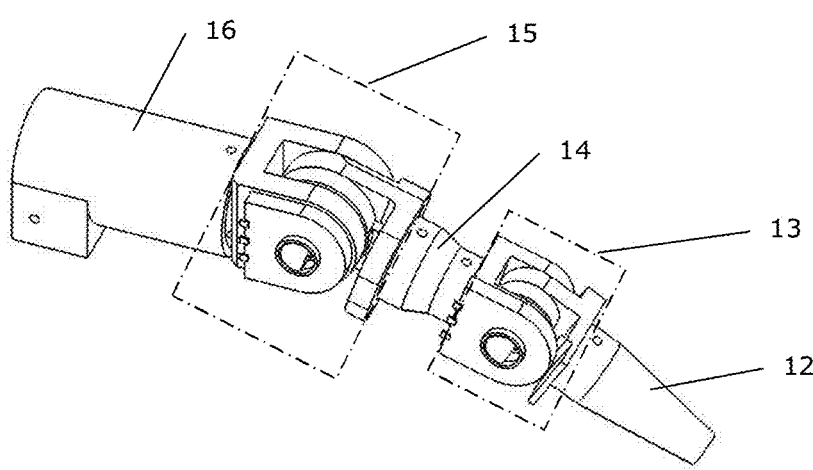
FIG. 3 is a schematic diagram of the index finger unit of a 32-degree-of-freedom bionic flexible endoskeletal dexterous hand provided by this application.
Figures 5, 6:
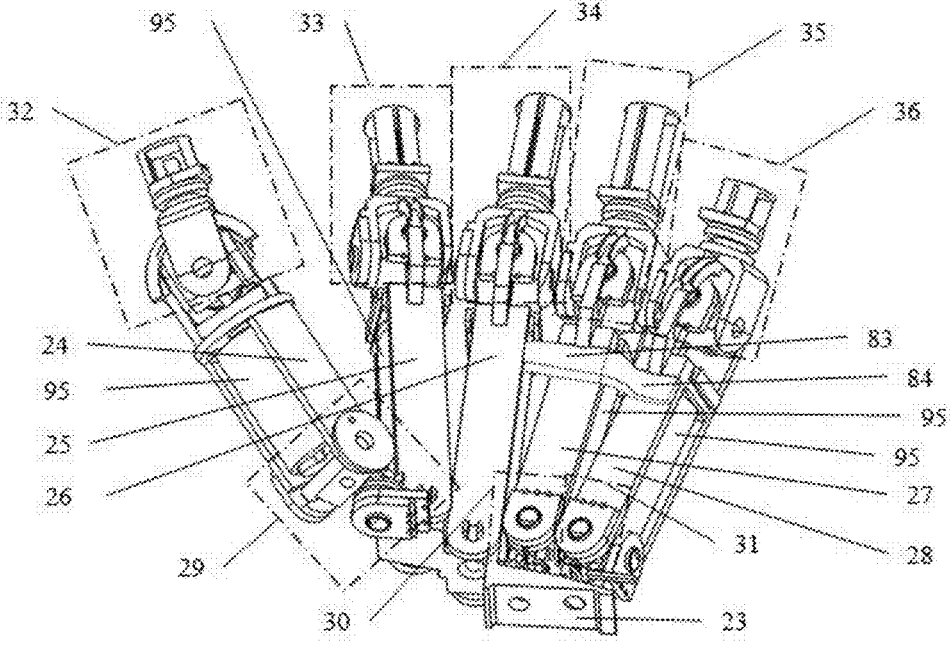
FIG. 5 is a schematic diagram of the palm unit of a 32-degree-of-freedom bionic flexible endoskeletal dexterous hand provided by this application.
FIG. 6 is a schematic diagram of a 3-degree-of-freedom metacarpophalangeal joint universal module of a 32-Dof bionic compliant endoskeletal dexterous hand provided by this application.

Referring to FIG. 1, the present invention proposes a 32-degree-of-freedom bionic endoskeletal dexterous hand, comprising a thumb unit 1, an index finger unit 2, a middle finger unit 3, a ring finger unit 4, a little finger unit 5, and a palm unit 6, a wrist module 7, and a forearm module 8, Referring to FIGS. 2 and 5, the thumb unit 1 comprises a thumb distal phalange 9; a thumb proximal phalange 11; and a thumb distal joint 10. The thumb unit is hinged with a thumb metacarpal 24 through a thumb metacarpophalangeal joint 32 with three degrees of freedom. Referring to FIGS. 3 and 5, the index finger unit 2 comprises an index finger distal phalange 12; an index finger middle phalange 14; an index finger proximal phalange 16; an index finger distal joint 13; and an index finger proximal joint 15, and is hinged with an index finger metacarpal 25 through an index finger metacarpophalangeal joint 33 with three degrees of freedom.

Referring to FIGS. 1 and 5, the middle finger unit 3 comprises a middle finger distal phalange; a middle finger middle phalange; a middle finger proximal phalange; a middle finger distal joint; and a middle finger proximal joint, and is hinged with a middle finger metacarpal 26 through a middle finger metacarpal joint 34 with three degrees of freedom.

The ring finger unit 4 comprises a ring finger distal phalange; a ring finger middle phalange; a ring finger proximal phalange; a ring finger distal joint; and a ring finger proximal joint, and is hinged with a ring finger metacarpal 27 through a ring finger metacarpophalangeal joint 35 with three degrees of freedom.

The little finger unit 5 comprises a little finger distal phalange; a little finger middle phalange; a little finger proximal phalange; a little finger distal joint; and a little finger proximal joint, and is hinged with a little finger metacarpal 28 through a little finger metacarpophalangeal joint 36 with three degrees of freedom.

The middle finger unit 3, the ring finger unit 4, and the little finger unit 5 are structurally similar to the index finger unit 2, as shown in FIG. 3, and no additional drawing description will be used here for illustration.

Referring to FIG. 5, the palm unit 6 comprises a carpometacarpal base 23; a thumb metacarpal 24; an index finger metacarpal 25; a middle finger metacarpal 26; a ring finger metacarpal 27; a little finger metacarpal 28; a thumb carpometacarpal joint 29; a ring finger carpometacarpal joint 30; a little finger carpometacarpal joint 31; a ring finger metacarpal flexible constraint element 83; a little finger metacarpal flexible constraint element 84; a thumb metacarpophalangeal joint 32; an index finger metacarpophalangeal joint 33; a middle finger metacarpophalangeal joint 34; a ring finger metacarpophalangeal joint 35; and a little finger metacarpophalangeal joint 36.

Figure 10:
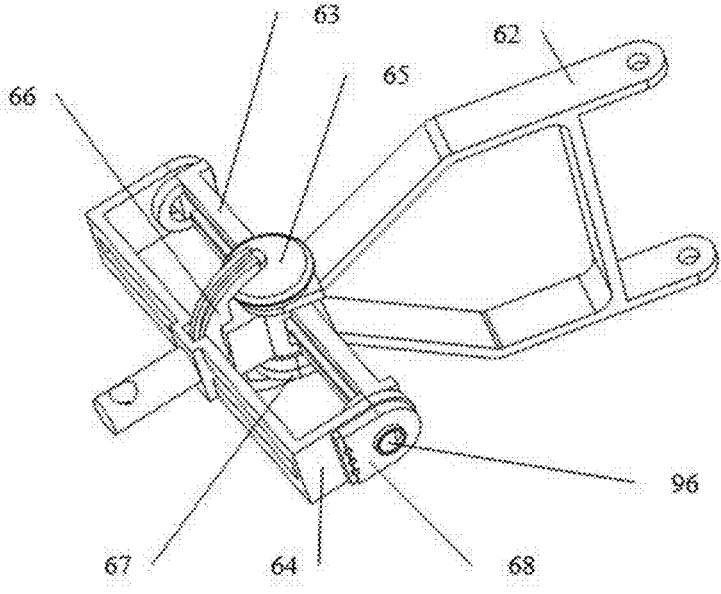
FIG. 10 is a schematic diagram of the wrist module of a 32-degree-of-freedom bionic flexible endoskeletal dexterous hand provided by this application.

Referring to FIG. 10, the wrist module 7 comprises a wrist joint and a wrist support frame 62.

Figure 11:
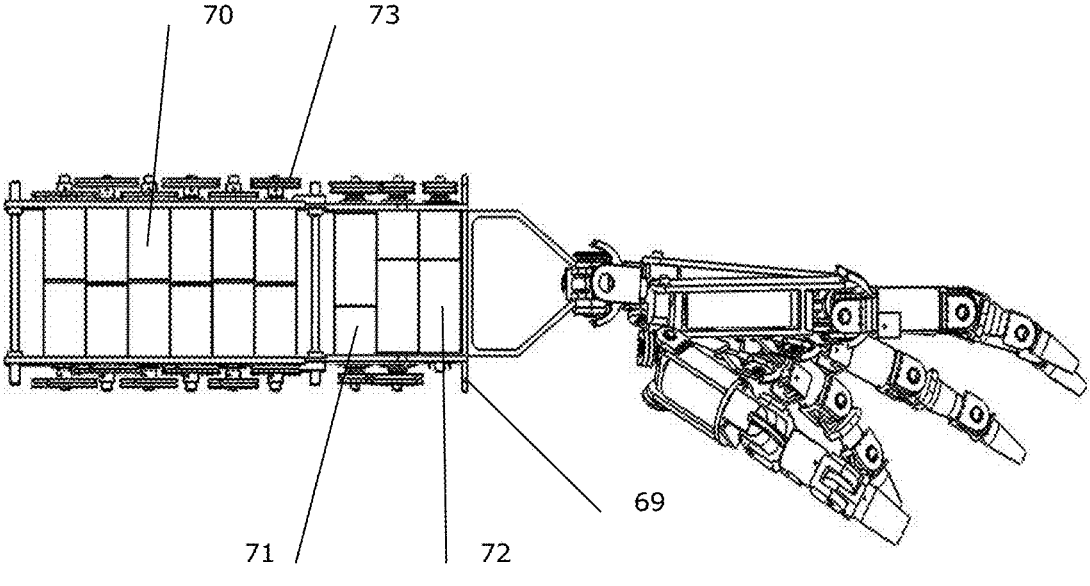
FIG. 11 is a side view of a 32-degree-of-freedom bionic flexible endoskeletal dexterous hand provided by this application.
Figure 12:
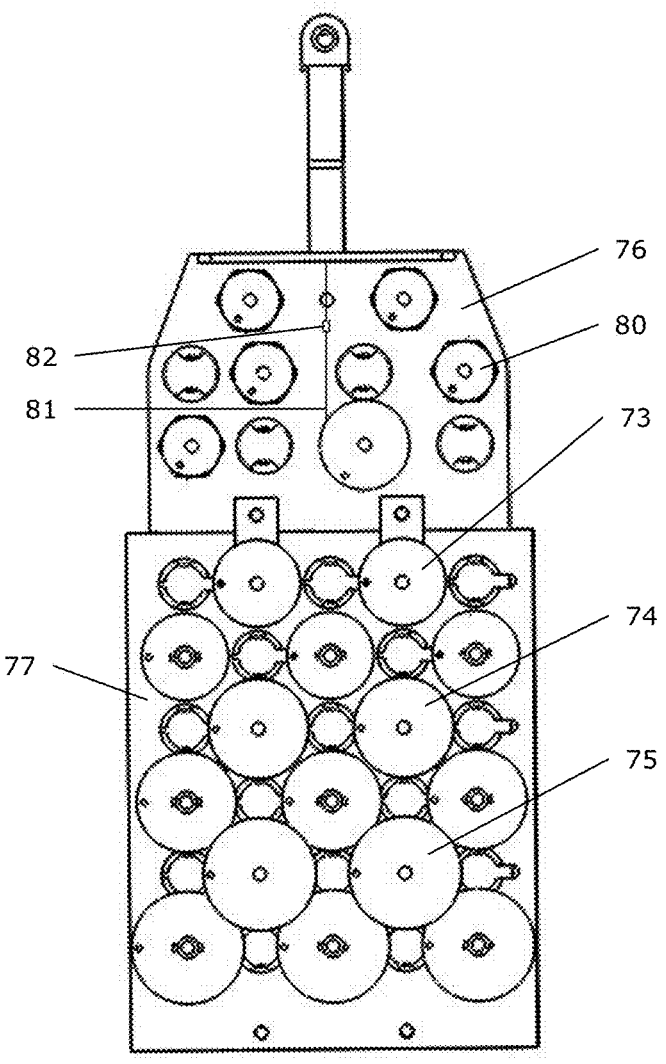
FIG. 12 is a top view of the forearm module of a 32-degree-of-freedom bionic flexible endoskeletal dexterous hand provided by this application embodiment.

Referring to FIGS. 11 and 12, the forearm module 8 comprises a tendon sheath guide base 69 and a actuator storage bin.

Referring to FIGS. 1, 2, 3, 5, the thumb unit 1 is hinged to the thumb metacarpal 24 through the thumb metacarpophalangeal joint 32.

The index finger unit 2 is hinged to the index finger metacarpal 25 through the index finger metacarpophalangeal joint 33.

The middle finger unit 3 is hinged to the middle finger metacarpal 26 through the middle finger metacarpophalangeal joint 34.

The ring finger unit 4 is hinged to the ring finger metacarpal 27 through the ring finger metacarpophalangeal joint 35.

The little finger unit 5 is hinged to the little finger metacarpal 28 through the little finger metacarpophalangeal joint 36.

A palm-internal actuator 95 is installed on each of the thumb metacarpal 24, the index finger metacarpal 25, the middle finger metacarpal 26, the ring finger metacarpal 27, and the little finger metacarpal 29. The thumb metacarpal 24, the index finger metacarpal 25, the middle finger metacarpal 26, the ring finger metacarpal 27, and the little finger metacarpal 29 are fixedly connected with the stator of the palm-internal actuator 95.

The thumb metacarpal 24 is hinged to the carpometacarpal base 23 through the thumb carpometacarpal joint 29.

The index finger metacarpal 25 is fixed to the carpometacarpal base 23.

The middle finger metacarpal 26 is fixed to the carpometacarpal base 23.

The ring finger metacarpal 27 is hinged to the carpometacarpal base 23 through the ring finger carpometacarpal joint 30.

The little finger metacarpal 28 is hinged to the carpometacarpal base 23 through the little finger carpometacarpal joint 31.

The ring finger metacarpal flexible constraint element 83 is configured to flexibly couple the middle finger metacarpal 26 with the ring finger metacarpal 27.

The little finger metacarpal flexible constraint element 84 is configured to flexibly couple the ring finger metacarpal 27 with the little finger metacarpal 28.

Referring to FIGS. 1, 5, and 10, the carpometacarpal base 23 is hinged to the wrist support frame 62 through the wrist joint.

The wrist support frame 62 is fixed to the forearm module 8.

The tendon sheath guide base 69 is installed at the joint of the wrist support frame 62 and the forearm module 8.

A plurality of forearm-internal actuators are installed in the actuator storage bin.

An actuator driving circuit is installed in the actuator storage bin.

Each forearm-internal actuator's output shaft is equipped with a respective capstan.

The palm-internal actuator 95 and the forearm-internal actuators are configured as rotary actuators.

The dexterous hand has 32 degrees of freedom, the thumb distal joint 10 has DOF of flexion/extension, the thumb metacarpophalangeal joint 32 has DOF of flexion/extension, DOF of abduction/adduction and DOF of circumduction, the thumb carpometacarpal joint 29 has DOF of circumduction and flexion, extension and DOF of abduction/adduction, the index finger distal joint 13 has DOF of flexion/extension, the index finger proximal joint 15 has DOF of flexion/extension, the index finger metacarpophalangeal joint 33 has DOF of flexion/extension, DOF of abduction/adduction, and DOF of circumduction, the middle finger distal joint has DOF of flexion/extension, the middle finger proximal joint has DOF of flexion/extension, the middle finger metacarpophalangeal joint 34 has DOF of flexion/extension, DOF of abduction/adduction, and DOF of circumduction, the ring finger distal joint has DOF of flexion/extension, the ring finger proximal joint has DOF of flexion/extension, the ring finger metacarpophalangeal joint 35 has DOF of flexion/extension, DOF of abduction/adduction, and DOF of circumduction, the ring finger carpometacarpal joint 30 has DOF of flexion/extension, and DOF of adduction/abduction, the little finger distal joint has DOF of flexion/extension, the little finger proximal joint has DOF of flexion/extension, the little finger metacarpophalangeal joint 36 has DOF of flexion/extension, DOF of abduction/adduction, and DOF of circumduction, the little finger carpometacarpal joint 31 has DOF of flexion/extension, and DOF of adduction/abduction, the wrist joint has DOF of flexion/extension, and DOF of abduction/adduction.

Preferably, the axes of the DOF of flexion/extension, DOF of abduction/adduction, and DOF of circumduction of the thumb metacarpophalangeal joint 32 are orthogonal, and the axes of the DOF of flexion/extension, the DOF of abduction/adduction and the DOF of circumduction of the index finger metacarpophalangeal joint 33 are orthogonal, and the axes of the DOF of flexion/extension, the DOF of abduction/adduction, and the DOF of circumduction of the middle finger metacarpophalangeal joint 34 are orthogonal, and the axes of the DOF of flexion/extension, the DOF of abduction/adduction, and the DOF of circumduction of the ring finger metacarpophalangeal joint 35 are orthogonal, and the axes of the DOF of flexion/extension, DOF of abduction/adduction, and DOF of circumduction of the little finger metacarpophalangeal joint 36 are orthogonal, and the axes of DOF of flexion/extension, DOF of adduction/abduction of the ring finger carpometacarpal joint 30 are orthogonal, and the axes of DOF of flexion/extension and DOF of abduction/adduction of the little finger carpometacarpal joint 31 are orthogonal, and the axes of DOF of flexion/extension and DOF of abduction/adduction of the wrist joint are orthogonal to control and calculation of motion planning.

DOF of circumduction of the thumb metacarpophalangeal joint 32, circumduction of the index finger metacarpophalangeal joint 33, circumduction of the middle finger metacarpophalangeal joint 34, circumduction of the ring finger metacarpophalangeal joint 35, circumduction of the little finger metacarpophalangeal joint 36, DOF of adduction/abduction of the ring finger carpometacarpal joint 30, and DOF of adduction/abduction of the little finger carpometacarpal joint 31 are passive degrees of freedom driven by external forces.

Referring to FIG. 5, DOF of abduction/adduction of the thumb metacarpophalangeal joint 32 is driven by the palm-internal actuator 95 installed on the thumb metacarpal 24 through a first gear train.

DOF of abduction/adduction of the index finger metacarpophalangeal joint 33 is driven by the palm-internal actuator 95 installed on the index finger metacarpal 25 through a second gear train.

DOF of abduction/adduction of the middle finger metacarpophalangeal joint 34 is driven by the palm-internal actuator 95 installed on the middle finger metacarpal 26 through a third gear train.

DOF of abduction/adduction of the ring finger metacarpophalangeal joint 35 is driven by the palm-internal actuator 95 installed on the ring finger metacarpal 27 through a fourth gear train.

DOF of abduction/adduction of the little finger metacarpophalangeal joint 36 is driven by the palm-internal actuator 95 installed on the little finger metacarpal 28 through a fifth gear train.

DOF of flexion/extension of the thumb distal joint 10, DOF of flexion/extension of the thumb metacarpophalangeal joint 32, flexion, extension and DOF of abduction/adduction and DOF of circumduction of the thumb carpometacarpal joint 29, DOF of flexion/extension of the index finger distal joint 13, DOF of flexion/extension of the index finger proximal joint 15, DOF of flexion/extension of the index finger metacarpophalangeal joint 33, DOF of flexion/extension of the middle finger distal joint, DOF of flexion/extension of the middle finger proximal joint, DOF of flexion/extension of the middle finger metacarpophalangeal joint 34, DOF of flexion/extension of the ring finger distal joint, DOF of flexion/extension of the ring finger proximal joint, DOF of flexion/extension of the ring finger metacarpophalangeal joint 35, DOF of flexion/extension of the ring finger carpometacarpal joint 30, DOF of flexion/extension of the little finger distal joint, DOF of flexion/extension of the little finger proximal joint, DOF of flexion/extension of the little finger metacarpophalangeal joint 36, DOF of flexion/extension of the little finger carpometacarpal joint 31, and DOF of flexion/extension and DOF of abduction/adduction of the wrist joint each is respectively driven by an antagonistic drive mechanism comprising a pair of the forearm-internal actuators, and are decoupled from each other, the antagonistic drive mechanism is driven by tendon.

Referring to FIGS. 1 and 12, the dexterous hand's one or more tendons 81 are covered with a plurality of tendon sheaths that protect and guide the tendon, the tendon sheaths comprise one to multiple layers from inside to outside.

Referring to FIGS. 1 and 11, the tendon sheath guide base comprises a plurality of tendon sheath mounting interfaces.

An end of each tendon sheath is fixed with a potential joint's joint base using tendon transmission, and an opposite end is fixed with the tendon sheath mounting interfaces of the tendon sheath guide base 69.

Figure 4:
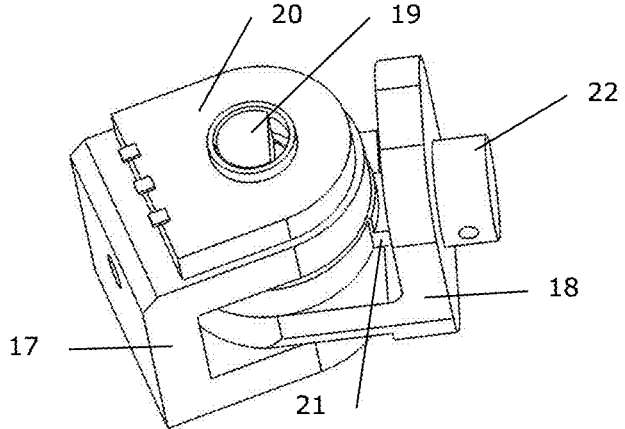
FIG. 4 is a schematic diagram of an 1-degree-of-freedom interphalangeal joint universal module of a 32-degree-of-freedom bionic compliant endoskeletal dexterous hand provided by this application.
Figure 13:
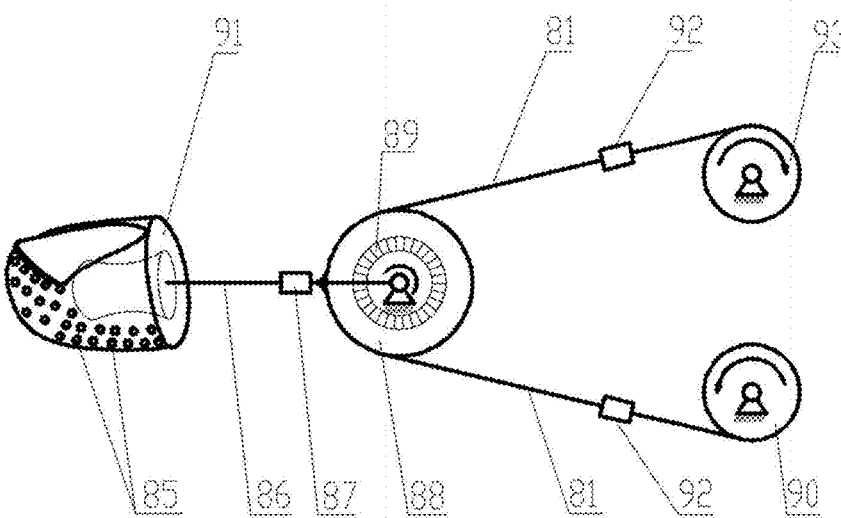
FIG. 13 is a schematic diagram of an antagonistic drive mechanism of a 32-degree-of-freedom bionic compliant endoskeletal dexterous hand provided by this application.

Referring to FIGS. 4 and 13, in the antagonistic drive mechanism, the rotational end of a controlled joint is fixedly connected to any point on the tendon 81 through a tendon fixing element 21, and the controlled degree of freedom of the controlled joint is jointly driven by a first forearm-internal actuator and a second forearm-internal actuator, the first forearm-internal actuator is configured to pull an end of the tendon 81 through a first corresponding capstan fixedly connected to the first forearm-internal actuator's output shaft, thereby pulling the rotational end of the controlled joint so that said rotational end has a movement trend in a direction of the controlled degree of freedom, the second forearm-internal actuator is configured to pull an opposite end of the tendon 81 through a second corresponding capstan fixedly connected to the second forearm-internal actuator's output shaft, thereby pulling the rotational end of the controlled joint so that said rotational end has a movement trend opposite to the direction of the controlled degree of freedom, thus constituting an antagonistic drive for the forearm-internal actuator.

Speed and output force of the first forearm-internal actuator and the second forearm-internal actuator that constitute the antagonistic drive are used to control motion, torque, joint damping and joint stiffness of the controlled joint.

Referring to FIG. 4, a 1-degree-of-freedom interphalangeal joint universal module is taken as an example. The tendon 81 is fixedly connected to the grooved pulley of the interphalangeal joint rotational end 18 through the tendon fixing element 21. The tendon fixing element 21 having a similar effect is also installed at the other joints' rotational ends.

Referring to FIG. 13, a forearm-internal actuator at the hand back side pulls the hand back side of the tendon 81 through the hand back side capstan 93. An forearm-internal actuator at the hand palm side pulls the hand palm side of the tendon 81 via the hand palm side capstan 90, constituting the antagonistic drive mechanism so as to pull the finger joint rotational end 88 together. Since for determining the movement trend of the joint, one only needs to refer to the movement of the dorsal capstan 93 and the palm capstan 90. Therefore, the forearm-internal actuators on the hand back side and on the hand palm side are hidden in FIG. 13.

1) When the forearm-internal actuator on the hand back side tightens the hand back side of the tendon 81, while the forearm-internal actuator in the hand palm side releases the hand palm side of the tendon 81, the finger joint rotational end 88 rotates toward the back of the hand, that is, stretching movement.

2) When forearm-internal actuator on the hand back side releases the hand back side of the tendon 81, while forearm-internal actuator on the hand palm side pulls the hand palm side of the tendon 81, the finger joint rotational end 88 rotates toward the hand palm side, that is, flexion movement.

When forearm-internal actuator on the hand back side applies a certain traction force through the hand back side of the tendon 81, and forearm-internal actuator on the hand palm side applies a certain traction force through the hand palm side of the tendon 81, the joint damping and joint stiffness at the turning end 88 of the finger joint can be controlled by dynamically adjusting the amount of traction on both hand sides to control. Dynamically adjusting the joint damping can make the finger joint rotational end 88 move in a smooth or explosive manner (such as playing a finger). Dynamically adjusting the joint stiffness of the finger joint rotational end 88 can prevent it from being affected by external force, or adapt to external force smoothly.

The antagonistic drive mechanism using said tendon transmission provides the basis for joint damping and joint stiffness control of the dexterous hand, enabling the dexterous hand to take into account the operational flexibility and anti-interference robustness.

Referring to FIG. 13, joint angle sensor 89 are installed at each joint of the dexterous hand to measure the rotation angle and angular velocity of each degree of freedom.

Joint force and torque sensors 87 are installed at all or part of the joints of the dexterous hand.

The dexterous hand's one or more tendons 81 are provided with tendon tension sensors 92.

The dexterous hand's one or more capstans are equipped with torque sensors to measure the torque in the capstan acted by each forearm-internal actuator's output shaft.

The joint base of each joint, which uses the tendon transmission, of the dexterous hand has respective tendon sheath mounting interfaces.

Referring to FIGS. 1, 2 and 3, the thumb distal phalange 9, the index finger distal phalange 12, the middle finger distal phalange, the ring finger distal phalange, the little finger distal phalange, the index finger middle phalange 14, the middle finger middle phalange, the ring finger middle phalange, the little finger middle phalange, the thumb proximal phalange 11, the index finger proximal phalange 16, the middle finger proximal phalange, and the ring finger proximal phalange and the little finger proximal phalange are configured with light alloy or light non-metallic material with electromagnetic shielding layers to shield internal circuits and improve the ability to resist electromagnetic interference.

The length ratio of the phalanges of the thumb unit 1, the index finger unit 2, the middle finger unit 3, the ring finger unit 4 and the little finger unit 5 are configured to simulate human hands.

The thumb distal phalange 9, the index finger distal phalange 12, the middle finger distal phalange, the ring finger distal phalange and the little finger distal phalange each is configured as a hollow structure, the outer wall can be adapted to finger force sensors or bionic skin 91, the hollow structure is with a tapered surface on an outer side wall and an open bottom surface, and the hollow structure is configured to accommodate the joint force and torque sensors as well as circuit and signal lines.

The index finger middle phalange 14, the middle finger middle phalange, the ring finger middle phalange and the little finger middle phalange each is configured as a hollow tube, and the hollow tube is configured to accommodate the joint force and torque sensors 22 as well as circuit and signal lines.

The thumb proximal phalange 11, the index finger proximal phalange 16, the middle finger proximal phalange, the ring finger proximal phalange and the little finger proximal phalange each is configured as a hollow tube with lateral projection at the base, the lateral projection is configured to accommodate metacarpophalangeal joint rotation angle sensor 43, and the hollow tube is configured to accommodate a circumduction reset device, the joint force and torque sensors 22 as well as the circuit and signal lines.

Referring to FIGS. 2, 3, 4, the thumb distal joint, the index finger distal joint 10, the middle finger distal joint 13, the ring finger distal joint, the little finger distal joint, the index finger proximal joint 15, the middle finger proximal joint, the ring finger proximal joint, the little finger proximal joint are respectively configured to use a 1-degree-of-freedom interphalangeal joint universal module.

The 1-degree-of-freedom interphalangeal joint universal module has DOF of flexion/extension, and comprises an interphalangeal joint base 17, an interphalangeal joint rotational end 18, an interphalangeal joint flexion/extension shaft 19, and interphalangeal joint flexion/extension angle sensor 20.

The interphalangeal joint flexion/extension shaft 19 has one or more first interfaces adapted to the interphalangeal joint flexion/extension angle sensor 20 and one or more second interfaces 18 locked to the interphalangeal joint rotational end.

The interphalangeal joint base 17 and the interphalangeal joint rotational end 18 each has a respective mounting interface for mounting the phalanges or the joint force and torque sensors 22.

Installation method of the interphalangeal joint base comprises any one of:

directly connecting the interphalangeal joint base 17 to the phalanges; and firstly fixedly connecting the interphalangeal joint base 17 to the joint force and torque sensor 22, and then fixing the joint force and torque sensor 22 to the phalanges (This method is used to measure one to multi-dimensional force and torque of the universal module with 1-degree-of-freedom interphalangeal joint universal module), and installation manner of the interphalangeal joint rotational end 18 comprises any one of:

directly connecting the interphalangeal joint rotational end 18 to the phalanges; and firstly fixedly connecting the interphalangeal joint rotational end 18 to the joint force and torque sensor 22, and then fixing the joint force and torque sensor 22 to the phalanges (This method is used to measure one to multi-dimensional force and torque of the universal module with 1-degree-of-freedom interphalangeal joint universal module).

Referring to FIG. 5, the carpometacarpal base 23 has an installation interface connected with the wrist joint, the thumb carpometacarpal joint 29, the ring finger carpometacarpal joint 30, the little finger carpometacarpal joint 31, the index finger metacarpal 25 and the middle finger metacarpal 26, and is configured as the main force bearing component of the palm unit 6.

Main axes of the index finger metacarpal 25 and the middle finger metacarpal 26 are installed at the carpometacarpal base 23, and are configured to form an included angle of 0 to 15 degrees, simulating a curved surface of a human hand palm.

The root of the ring finger metacarpal 27 and the ring finger carpometacarpal joint form an evolute pair of DOF of adduction/abduction.

The root of the palmar phalange 28 of the little finger and the palmar joint 31 of the little finger form a evolute pair of DOF of adduction/abduction.

The thumb metacarpal (24)'s root is configured to cooperate with the thumb carpometacarpal joint 29 to form a first evolute pair with DOF of flexion/extension and DOF of abduction/adduction, and is fixed to a V-shape groove pulley used for the tendon transmission.

Figure 7:
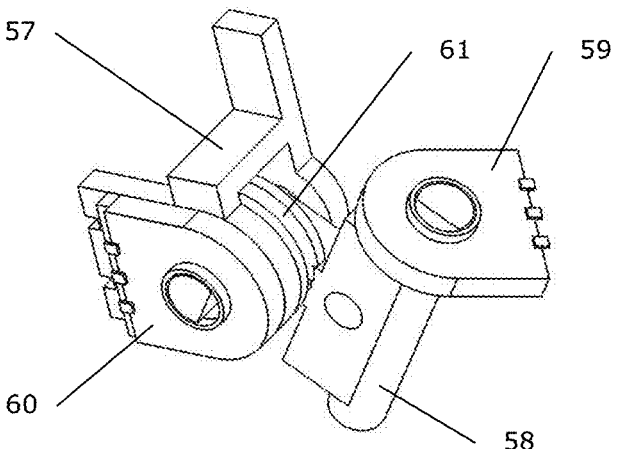
FIG. 7 is a schematic diagram of the thumb carpometacarpal joint of a 32-degree-of-freedom bionic flexible endoskeleton dexterous hand provided in this application.

Referring to FIG. 7, flexion, extension and DOF of abduction/adduction of the thumb carpometacarpal joint 29 is 1-degree-of-freedom, and couples DOF of flexion/extension and DOF of abduction/adduction, the axis of flexion, extension and DOF of abduction/adduction of the thumb carpometacarpal joint 29 and the axis of DOF of abduction/adduction of the thumb metacarpophalangeal joint 32 are configured to form an included angle of 30 to 60 degrees, simulating the motion pattern of flexion/extension and abduction/adduction of the thumb carpometacarpal joint when the hand is doing a opposition movement, so as to realize a opposition function.

The thumb carpometacarpal joint 29 comprises a thumb carpometacarpal joint base 57, a thumb carpometacarpal joint rotational end 58, thumb carpometacarpal joint rotation angle sensor 60, and thumb carpometacarpal joint flexion, extension and abduction/adduction angle sensor 59.

An end of the thumb carpometacarpal joint rotational end 58 and the thumb carpometacarpal joint base 57 form a revolute pair with DOF of circumduction, and is coaxially fixed with a V-shape groove pulley 61 used for tendon transmission. An opposite end of the thumb carpometacarpal rotational end and the thumb metacarpal form a second evolute pair with flexion, extension and DOF of abduction/adduction, and is provided with a shaft that forms flexion/extension and DOF of abduction/adduction with the thumb palm phalange 24, and is fixedly connected with the rotator of the thumb carpometacarpal joint flexion, extension, and abduction/adduction angle sensor 59. The fixator of the flexion, extension, and abduction/adduction angle sensor 59 is fixedly connected with the thumb metacarpal 24.

The thumb carpometacarpal rotational end comprises the tendon sheath mounting interfaces.

Referring to FIG. 5, the ring finger metacarpal flexible constraint element 83 flexibly connects the middle finger metacarpal 26 and the ring finger metacarpal 27, and can be installed between the middle finger metacarpal 26 and the ring finger metacarpal 27 or on the hand palm side of the middle finger metacarpal 26 and the ring finger metacarpal 27. The ring finger metacarpal flexible constraint element is configured to restrain movement range of the ring finger metacarpal 27, and to keep the ring finger metacarpal 27 in place (i.e., the resting position) when there is no external force. When the ring finger metacarpal 27 is performing flexion movement, the ring finger metacarpal flexible constraint element 83 holds the ring finger metacarpal and adduction motion occurs incidentally.

The little finger metacarpal flexible constraint element 84 flexibly connects the ring finger metacarpal 27 and the little finger metacarpal 28, and can be installed between the ring finger metacarpal 27 and the little finger metacarpal 28 or on the hand palm side of the ring finger metacarpal 27 and the little finger metacarpal 28. The little finger metacarpal flexible constraint element 84 is configured to restrain movement range of the little finger metacarpal 28, and to keep the little finger metacarpal 28 in place (i.e., the resting position) when there is no external force, when the little finger metacarpal 28 is performing flexion movement, the little finger metacarpal flexible constraint element 84 holds the little finger metacarpal 28 and the adduction motion occurs incidentally.

When the palm unit (i.e., the hand palm) is subjected to external forces from little finger side to thumb side (such as during a handshake), the adduction motion of the ring finger metacarpal 27 and the little finger metacarpal 28 can occur simultaneously, and the ring finger metacarpal flexible constraint element 83 and the ring finger metacarpal flexible constraint element 84 absorbs and cushions said external forces.

The ring finger metacarpal flexible constraint element 83 and the little finger metacarpal flexible constraint element 84 can be made of flexible materials (such as rubber or silicone).

Figure 8:
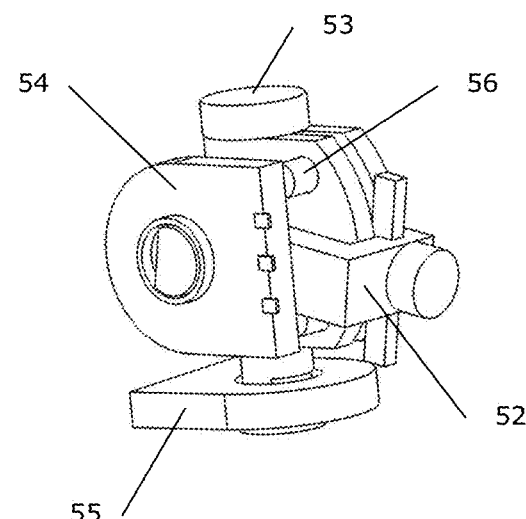
FIG. 8 is a schematic diagram of the ring finger carpometacarpal joint of a 32-degree-of-freedom bionic flexible endoskeleton dexterous hand provided in this application.

Referring to FIG. 8, the ring finger carpometacarpal joint 30 has DOF of flexion/extension and DOF of adduction/abduction. The ring finger carpometacarpal joint 30 comprises a ring finger carpometacarpal joint base 52, a ring finger carpometacarpal rotational end 53, ring finger carpometacarpal joint rotation angle sensor 54, and ring finger carpometacarpal joint limiting pin 56, and little finger carpometacarpal joint abduction/adduction angle sensor 55.

Figure 9:
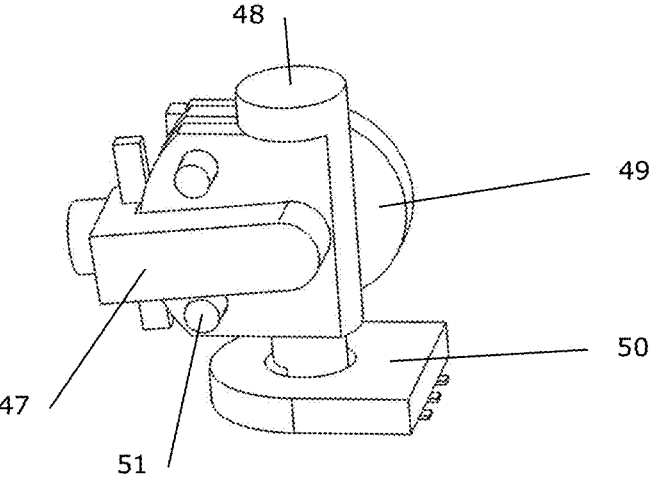
FIG. 9 is a schematic diagram of the little finger carpometacarpal joint of a 32-degree-of-freedom bionic flexible endoskeleton dexterous hand provided in this application.

Referring to FIG. 9, the little finger carpometacarpal joint 31 has DOF of flexion/extension and DOF of abduction/adduction, and comprises a little finger carpometacarpal joint base 47, a little finger carpometacarpal rotational end 48, little finger carpometacarpal joint rotation angle sensor 49, and little finger carpometacarpal limiting pin 51, little finger carpometacarpal joint abduction/adduction angle sensor 50.

Referring to FIGS. 4, 5, and 6, the thumb metacarpophalangeal joint 32, the index finger metacarpophalangeal joint 33, the middle finger metacarpophalangeal joint 34, the ring finger metacarpophalangeal joint 35, the little finger metacarpophalangeal joint 36 are respectively configured to use a 3-degree-of-freedom metacarpophalangeal joint universal module.

The 3-degree-of-freedom metacarpophalangeal joint universal module has DOF of flexion/extension, DOF of abduction/adduction, and DOF of circumduction, the axes of said DOF of flexion/extension, DOF of abduction/adduction, and DOF of circumduction are orthogonal to facilitate control and calculation of motion planning.

The 3-degree-of-freedom metacarpophalangeal joint universal module comprises a metacarpophalangeal joint abduction/adduction rotational end 37, a metacarpophalangeal joint abduction/adduction shaft 40, a metacarpophalangeal joint flexion/extension rotational end 38, a metacarpophalangeal joint flexion/extension shaft 39, a circumduction reset device, metacarpophalangeal joint flexion/extension angle sensor 42, metacarpophalangeal joint abduction/adduction angle sensor 41, metacarpophalangeal joint rotation angle sensor 43, and a metacarpophalangeal joint tendon guide groove 94.

The cylindrical surface of the metacarpophalangeal joint abduction/adduction shaft 40 has a gap to fix with and fit with the metacarpophalangeal joint flexion/extension shaft 39, and an end thereof has a first interface adapted to the metacarpophalangeal joint abduction/adduction angle sensor 41.

The cylindrical surface of the metacarpophalangeal joint flexion/extension shaft 39 has a gap to fix with and fit with the metacarpophalangeal joint abduction/adduction shaft 40, and an end thereof has a second interface 42 adapted to the metacarpophalangeal joint flexion/extension angle sensor.

The metacarpophalangeal joint flexion/extension rotational end 38 comprises a rotational joint base 97 that supports the distal phalanges to perform rotational motion and bears force, The circumduction reset device is installed at the rotation joint base 97 of the metacarpophalangeal joint flexion/extension rotational end 38.

The circumduction reset device comprises a supporting shaft 44, a spring clamping element 45 and an elastic reset element 46 (such as a reset spring). The supporting shaft 44 is fixedly connected with the rotation joint base 97 of the metacarpophalangeal joint flexion/extension rotational end 38. The spring clamping element 45 is fixedly connected with the inner wall of the respective finger unit's proximal phalange. The elastic reset element 46 (such as a reset spring) is clamped between the supporting shaft 44 and the spring clamping element 45, so that the finger units perform the rotational motion when subjected to external torsion, and the amplitude of the rotational motion is positively related to said external torsion, and when the external torsion disappears, the finger units returns to original position (i.e., the resting position) thereof.

The circumduction reset device has a third interface for installing a strain gauge or the joint force and torque sensor 22, so as to measure one to multi-dimensional forces and torques of the 3-degree-of-freedom metacarpophalangeal joint universal module. For example, the strain gauge may be mounted on the outer surface of the elastic reset element 46.

The metacarpophalangeal joint tendon guide groove 94 is fixedly connected to the metacarpophalangeal joint abduction/adduction rotational end, and tendon and the tendon sheaths passing the metacarpophalangeal joint adhere to the metacarpophalangeal joint tendon guide groove to slide, the metacarpophalangeal joint tendon guide groove 94 is configured to guide the direction of the tendon 81 and tendon sheaths so as to reduce the interference of the metacarpophalangeal joint on the tendon 81 that drives the DOF of flexion/extension of the metacarpophalangeal joint, and the interference of the metacarpophalangeal joint on the tendon sheath that spans the 3-degree-of-freedom metacarpophalangeal joint universal module, the lateral section of the metacarpophalangeal joint tendon guide groove 94 is semicircular, the tendon 81 maintains a constant transmission arm length during transmission (which is equal to the radius of the metacarpophalangeal joint tendon guide groove 94).

Referring to FIGS. 5 and 6, a respective palm-internal actuator 95 installed on any one of the thumb metacarpal 24, the index finger metacarpal 25, the middle finger metacarpal 26, the ring finger metacarpal 27, and the little finger metacarpal 28 is configured to drive the respective metacarpophalangeal joint abduction/adduction rotational end 37 hinged to respective metacarpal through the respective gear train to perform abduction/adduction motion.

Referring to FIG. 10, the axis of the DOF of abduction/adduction and DOF of flexion/extension of the wrist joint are orthogonal, which is conducive to the calculation of control and motion planning.

The wrist joint comprises a wrist joint abduction/adduction rotational end 63, a wrist joint abduction/adduction shaft 65, a wrist joint flexion/extension rotational end 64, a wrist joint flexion/extension shaft 96, wrist joint abduction/adduction angle sensor 67, wrist joint flexion/extension angle sensor 68 and a wrist joint tendon guide groove 66.

An end of the wrist joint abduction/adduction shaft 65 is provided with a coaxial driven V-shape groove pulley, a middle part of the wrist joint abduction/adduction shaft has a gap for locking and matching with the wrist joint flexion/extension shaft 96, and an opposite end of the wrist joint abduction/adduction shaft comprises a first interface adapted to the wrist joint abduction/adduction angle sensor 67.

The cylindrical surface of the wrist joint flexion/extension shaft 96 has a gap to fix with and fit with the wrist joint abduction/adduction shaft 65, and an end thereof comprises a second interface adapted to the wrist joint flexion/extension angle sensor 68.

The wrist joint flexion/extension rotational end 64 comprises a third interface connected with the carpometacarpal base 23, and a fourth interface for installing the joint force and torque sensor 87 (to measure one to multi-dimensional forces and torques of the wrist).

The wrist joint tendon guide groove 66 is fixedly connected to the wrist joint abduction/adduction rotational end 63, and the tendon 81 driving the wrist joint's DOF of flexion/extension adheres to the wrist joint tendon guide groove 66 to slide, so as to attenuate the interference of the tendons 81 that drive the DOF of flexion/extension of the wrist joint during the abduction/adduction motion of the wrist joint, the side section of the wrist joint tendon guide groove 66 is semi-circular, so as to make the tendon maintain a constant transmission arm length during transmission (which is equal to the radius of the wrist joint tendon guide groove 66).

The wrist support frame 62 comprises the tendon sheath mounting interfaces, a wrist joint base, and a forearm mounting base, used for coupling the wrist joint and the forearm module 8 together.

Referring to FIGS. 5 and 6, an improved solution is that each palm-internal actuator 95 is configured to use linear actuators, and to drive a respective metacarpophalangeal joint abduction/adduction rotational end 37 through a hinged linkage mechanism to perform abduction/adduction motion.

An improved solution is that each forearm-internal actuator is configured to use linear actuators, and each forearm-internal actuator's output shaft is fixedly connected to the tendon 81.

Another improved solution is that each forearm-internal actuator is configured to use rotary actuators, and each forearm-internal actuator's output shaft is not fixedly connected to the tendon, a screw mechanism is used to convert the rotary motion of each forearm-internal actuator's output shaft into a linear motion, each forearm-internal actuator's output shaft is fixedly connected to the screw mechanism's screw, and the screw mechanism's linear motion end of is fixed to the tendon 81.

If the forearm-internal actuators each adopts a rotary actuator, a servo, a DC motor or a brushless motor can be used. If the inner actuator of the forearm adopts a linear actuator, artificial muscles or linear motors can be used.

Referring to FIGS. 1, 5, 11, and 12, the forearm-internal actuators are divided into the main joint actuators 70, auxiliary joint actuators 71, and wrist joint actuators 72 according to the magnitude of the peak output force or peak output torque and the driving object. In terms of the magnitude of the peak output force or peak output torque, the main joint actuators (70)' is the smallest, the auxiliary joint actuators (71)' is in the middle, and the wrist joint actuators (72)' is the largest.

The main joint actuators 70 are used to drive the DOF of flexion/extension of the thumb distal joint 10, the DOF of flexion/extension of the thumb metacarpophalangeal joint 32, the flexion, extension and DOF of abduction/adduction of the thumb carpometacarpal joint 29, the DOF of flexion/extension of the index finger distal joint 13, the DOF of flexion/extension of the index finger proximal joint 15, the DOF of flexion/extension of the index finger metacarpophalangeal joint 33, the DOF of flexion/extension of the middle finger distal joint, the DOF of flexion/extension of the middle finger proximal joint, the DOF of flexion/extension of the middle finger metacarpophalangeal joint 34, the DOF of flexion/extension of the ring finger distal joint, the DOF of flexion/extension of the ring finger proximal joint, the DOF of flexion/extension of the ring finger metacarpophalangeal joint 35, the DOF of flexion/extension of the little finger distal joint, the DOF of flexion/extension of the little finger proximal joint, and the DOF of flexion/extension of the little finger metacarpophalangeal joint 36.

The auxiliary joint actuators 71 are used to drive the DOF of circumduction of the thumb carpometacarpal joint 29, the DOF of flexion/extension of the ring finger carpometacarpal joint 30, and the DOF of flexion/extension of the little finger carpometacarpal joint 31.

The wrist joint actuators 72 are used to drive the DOF of flexion/extension of the wrist joint and the DOF of abduction/adduction.

The layout of some or all of the forearm-internal actuators in the forearm module 8 includes one or more of:

installing some or all of the forearm-internal actuators in multiple rows from the thumb side to the little finger side; and/or installing some or all of the forearm-internal actuators in multiple rows from the hand side to the elbow side; and/or dividing some or all of the forearm-internal actuators into a plurality of pairs, each pair is configured to drive a respective degree of freedom to form the antagonistic drive, a mounting method for each pair comprises:

installing the respective forearm-internal actuators of each pair in the opposite direction, the respective forearm-internal actuators comprise a respective first shaft forearm-internal actuator and a respective second forearm-internal actuator, the respective first shaft forearm-internal actuator's output shaft is facing hand back side and the respective second shaft inner output shaft's output shaft is facing hand palm side; or installing the respective forearm-internal actuators of each pair in the opposite direction, the respective first shaft forearm-internal actuator's output shaft is facing the thumb side of the hand and the respective second shaft inner output shaft's output shaft is facing the little finger side; or installing the respective forearm-internal actuators of each pair in the same direction, with the respective forearm-internal actuators' output shaft facing the hand back side; or installing the respective forearm-internal actuators of each pair in the same direction, with the respective forearm-internal actuators' output shaft facing the hand palm side; or installing the respective forearm-internal actuators of each pair in the same direction, with the respective forearm-internal actuators' output shaft facing the thumb side; or installing the respective forearm-internal actuators of each pair in the same direction, with the respective forearm-internal actuators' output shaft facing the little finger side.

Preferably, in order to make full use of the space in the forearm module 8, some or all of the forearm-internal actuators in the forearm module 8 adopt the following layout:

1) The wrist joint actuator 72 is placed in the actuator storage bin closest to the wrist joint. A set of wrist joint actuators 72 that drive the DOF of abduction/adduction of the wrist joints are installed in the same direction. The output shaft is facing the hand back side. A set of wrist joint actuators that drive the wrist joint's DOF of flexion/extension are installed facing each other, with the output shaft facing the hand back side and hand palm side, respectively.

2) The main joint actuators 70 are placed in the actuator storage bin away from the wrist joint. The main joint actuators 70 of each group are installed facing each other, and is divided into the main joint actuators facing the hand palm side and the main joint actuators driving to the hand back side, that is, the output shaft of main joint actuators facing the hand palm side faces the palm side of the hand, while the output shaft of main joint actuators facing the hand back side faces the back side of the hand.

3) The auxiliary joint actuators 71 are placed between the wrist joint actuator and the main joint actuator. The auxiliary joint actuators 71 of each group are installed facing each other, and the output shaft faces the hand back side and the hand palm respectively.

4) The main joint actuators 70 are arranged in 5 columns from the thumb side to the little finger side, and each column corresponds to a finger unit, that is, starting from the thumb side, the first column corresponds to the thumb unit, the second column corresponds to the index finger unit, the third column corresponds to the middle finger unit, the fourth column corresponds to the ring finger unit, and the fifth column corresponds to the little finger unit.

Each column of the main joint actuators 70 is arranged in three groups from the hand side to the elbow side (there are a total of 6 columns). Each group includes a pair of the main joint actuators 70 that collectively drive 1 degree of freedom of the corresponding finger unit in the column. That is, starting from the hand side, the first group of column 1 drives the flexion, extension and DOF of abduction/adduction of the thumb carpometacarpal joint 29, the second group of column 1 drives the flexion/extension of the thumb metacarpophalangeal joint 32, and the third group of column 1 drives the flexion/extension of the thumb distal joint 10. The first group of column 2 drives the flexion/extension of the index finger metacarpophalangeal joint 33, the second group of column 2 drives the DOF of flexion/extension of the index finger proximal joint 15, the third group of column 3 drives the DOF of flexion/extension of the index finger distal joint 13. The first group of column 3 drives the DOF of flexion/extension of the middle finger metacarpophalangeal joint 34, the second group of column 3 drives the DOF of flexion/extension of the middle finger proximal joint, and the third group of column 3 drives the DOF of flexion/extension of the middle finger distal joint. The first group of column 4 drives the DOF of flexion/extension of the ring finger metacarpophalangeal joint 35, the second group of column 4 drives the DOF of flexion/extension of the ring finger proximal joint, and the third group of column 4 drives the DOF of flexion/extension of the ring finger distal joint.

The first group of column 5 drives the DOF of flexion/extension of the little finger metacarpophalangeal joint 36, the second group of column 5 drives the DOF of flexion/extension of the little finger proximal joint, and the third group of column 5 drives the DOF of flexion/extension of the little finger distal joint.

The forearm module's capstans each has one or more diameters, and each of the forearm module's capstans is respectively distributed on the forearm module's hand back side, forearm module's hand palm side, forearm module's thumb side, or the forearm module's little finger side, and some or all of the capstans on each side are divided into one to multiple layers.

Preferably, in order to make full use of the space in the forearm module 8, a large number of capstans are integrated into the compact forearm module to provide suitable motion range for each joint, and to avoid the large number of capstans and tendons 81 to interfere with each other. Some or all of the capstans in the forearm module 8 has the following layout:

1) Four kinds of capstans with different diameters are used. They are divided into type I capstan 80, type II capstan 73, type III capstan 74 and type IV capstan 75 according to the diameter of the capstan.

2) The DOF of flexion/extension of the thumb distal joint 10, DOF of flexion/extension of the index finger distal joint 13, DOF of flexion/extension of the middle finger distal joint, DOF of flexion/extension of the ring finger distal joint, and DOF of flexion/extension of the little finger distal joint are configured to be driven by said type IV capstan 75.

3) The DOF of flexion/extension of the thumb metacarpophalangeal joint 32, the DOF of flexion/extension of the index finger proximal joint 15, the DOF of flexion/extension of the middle finger proximal joint, the DOF of flexion/extension of the ring finger proximal joint, and the DOF of flexion/extension of the little finger distal joint are configured to be driven by said type III capstan 74.

4) The flexion, extension and DOF of abduction/adduction of the thumb carpometacarpal joint 29, the DOF of flexion/extension of the index finger metacarpophalangeal joint 33, the DOF of flexion/extension of the middle finger metacarpophalangeal joint 34, the DOF of flexion/extension of the ring finger metacarpophalangeal joint 35, and the DOF of flexion/extension of the little finger metacarpophalangeal joint 36 are configured to be driven by said type II capstan 73.

5) The DOF of circumduction of the thumb carpometacarpal joint 29, the DOF of flexion/extension of the ring finger carpometacarpal joint 30, the DOF of flexion/extension of the wrists of the little finger carpometacarpal joint 31, and the DOF of flexion/extension of the wrist joint and the DOF of abduction/adduction are configured to be driven by said type I capstan 80.

6) The capstans of the main joint actuators facing the hand palm side on column 1, column 3, column 5 are installed on the inner layer of the hand palm side of the forearm module 8. The capstans of the main joint actuators facing hand palm side on column 2 and column 4 are installed on the outer layer of the hand palm side of the forearm module.

7) The capstans of the main joint actuators facing the hand back side on column 1, column 3, column 5 are installed on the outer layer of the hand back side of the forearm module 8. The capstans of the main joint actuators facing hand palm side on column 2 and column 4 are installed on the inner layer of the hand back side of the forearm module. The actuator storage bin comprises one or more sub storage bins, if the number of the sub storage bins is more than one, sub storage bins can be disassembled or assembled with each other, which is convenient for each sub storage bin to be independently assembled, debugged and maintained.

As shown in FIGS. 1, 11 and 12, in one embodiment of this application, the actuator storage bin comprises a front sub-storage bin and a rear sub-storage bin.

The front sub-storage bin comprises the upper front receiving panel 76, the lower front receiving panel 78 and the connecting parts, the internal installation of a plurality of the auxiliary joint actuators 71 and a plurality of the wrist joint actuators 72.

The external surface of the hand back side of the upper front receiving panel 76 and the external surface of the hand palm side of the lower front receiving panel 78 are laid with the power cord of each auxiliary joint actuator 71 and each wrist joint actuator 72.

The rear sub-storage bin comprises the upper rear receiving panel 77, the lower rear receiving panel 79 and the connection parts, its internal installation is provided with a plurality of main joint actuators 70.

The external surface of the hand back side of the upper rear receiving panel 77 and the external surface of the hand palm side of the lower rear receiving panel 79 are laid with the power cord of each major joint actuator 70.

The front sub-storage bin and the rear sub-storage bin can be separated or assembled together, so that the front sub-storage bin and the rear sub-storage bin can be independently assembled, debugged and maintenance.

Referring to FIGS. 1, 11, and 12, the plurality of tendon sheath mounting interfaces of the tendon sheath guide base are respectively distributed on the back side and the palm side of the tendon sheath guide 69, the plurality of tendon sheath mounting interfaces on each side are arranged in one to multiple layers for fixing tendon sheath and guide tendon 81, so that multiple tendons 81 and tendon sheaths can smoothly cross the wrist module to each joint of the hand module, reducing mutual interference, and the tendon sheath guide 69 has a first interface adapted to the wrist support frame 62 and a second interface adapted to the forearm module 8.

The one or more tendon sheaths of the dexterous hand are respectively mounted at the end of each tendon sheath by a detachable tendon sheath fixing element on the tendon sheath mounting interfaces of the tendon sheath guide base 69, and the one or more tendon sheaths of the dexterous hand are respectively mounted at the opposing end of each tendon sheath on the tendon sheath mounting interfaces of the joint base of the joints using tendon transmission through the detachable tendon sheath fixing element.

The tendon sheath fixing element enables the tendon sheath to be easily installed or removed from the tendon sheath guide 69.

Due to the large number of tendons and tendon sheaths, in order to make the attached Figures clear and intuitive, only part of one tendon 81 is shown in FIG. 12, while the rest tendons and tendon sheaths have been hidden.

Referring to FIG. 12, the tendon's (8) part, which is between the capstan and the tendon sheath guide 69, is provided with a tendon coupling 82, the tendon coupling 82 can be disconnected or coupled so that the tendon 81 is disconnected or coupled from the middle of the tendon, and the maximum outer diameter of the tendon coupling 82 is smaller than the inner diameter of each tendon sheath mounting interface of the tendon sheath guide base 59, so that the tendon coupling 82 can pass through the tendon sheath mounting interface along with the tendon 81. The tendon coupling 82 can be composed of two sub-parts and connected together by thread.

The dexterous hand uses the tendon sheath fixing element and tendon coupling 82, so that the hand module and the wrist module of the dexterous hand can be assembled with the forearm module 8 or separated conveniently, which is convenient for production and maintenance.

The thumb distal joint 10, the thumb metacarpophalangeal joint 32, the index finger distal joint 13, the index finger proximal joint 15, the index finger metacarpophalangeal joint, the middle finger distal joint, the middle finger proximal joint, the middle finger metacarpophalangeal joint 34, the ring finger distal joint, the ring finger proximal joint, the ring finger metacarpophalangeal joint 35, the little finger distal joint, the little finger proximal joint, the little finger metacarpophalangeal joint 36 each comprises a type I tendon sheath restraint element. The type I tendon sheath restraint element can be made of flexible material into a flexible sleeve.

The wrist joint is equipped with a type II tendon sheath restraint element. The type II tendon sheath restraint element can be made of flexible material into a flexible sleeve with multi-layer internal partition.

The thumb metacarpal 24, the index finger metacarpal 25, the middle finger metacarpal 26, the ring finger metacarpal 27, the little finger metacarpal 28 each is equipped with a type III tendon sheath restraint element on the upper surface and the lower surface thereof. The type III tendon sheath restraint element can be made into a through pipe or groove with multiple layers of internal partition.

A type IV tendon sheath restraint element is installed on each of the index finger proximal phalange's (16) hand back side and hand palm side, the middle finger proximal phalange, the ring finger proximal phalange, the little finger proximal phalange. The type IV tendon sheath restraint element can use the through pipe with smooth inner wall. The tendon sheath can slide axially in the type IV tendon sheath restraint element.

The type I tendon sheath restraint element is a first flexible element that can flex, and comprises one or more type I tendon sheath restraint element's guide grooves or first guide holes for guiding one to four of the tendon sheaths to slide along respective axes thereof.

The type II tendon sheath restraint element is a second flexible element that can flex, comprises one or more type II tendon sheath restraint element's guide grooves or guide holes for guiding at least five of the tendon sheaths to slide along respective axes thereof, and has a structure allowing one or more of the tendon sheaths that pass through the type II tendon sheath restraint element to curl respectively inside the type II tendon sheath restraint element.

The type III tendon sheath restraint element comprises one or more type III tendon sheath restraint element's guide grooves or guide holes for guiding one or more of the tendon sheaths to slide along respective axes thereof, and has a structure allowing one or more of the tendon sheaths that pass through the type III tendon sheath restraint element to curl respectively inside the type II tendon sheath restraint element.

The type IV tendon sheath restraint element comprises one or more type IV tendon sheath restraint element's guide grooves or guide holes for guiding one or more of the tendon sheaths to slide along respective axes thereof.

The dexterous hand is configured to adopt a tendon transmission layout comprising:

1) Distributing a plurality of the tendons 81 on the dexterous hand's hand back side and hand palm side, an end of the plurality of the tendons is fixedly connected to a corresponding capstan, a starting end of the tendon sheath of the plurality of the tendons is fixed to the tendon sheath mounting interfaces on the tendon sheath guide base's hand back side and hand palm side through a tendon sheath fixing element, respectively, the plurality of the tendons 81 are passing through said tendon sheath mounting interfaces and extend towards the wrist module 7, 2) the tendons 81, that drive the wrist joint, are configured to pass the wrist support framework 6's tendon sheath mounting interfaces through the tendon sheaths thereof, the tendons that drive the wrist joint are respectively connected to a wrist joint abduction/adduction rotational end 63 and a wrist joint flexion/extension rotational end 64, the tail ends of the tendon sheaths thereof are fixedly connected to the wrist support framework's tendon sheath mounting interfaces 62 through the tendon sheath fixing element, 3) other tendons 82 and the tendon sheaths thereof are configured to pass the wrist joint at the dexterous hand's hand back side and hand palm side respectively, and directions and curling spaces of said other tendons and of the tendon sheaths of said other tendons are restrained by large joint's tendon sheath flexible restraint elements installed at the wrist module, said other tendons and the tendon sheaths thereof are then configured to converge at the carpometacarpal base's hand back side and hand palm side 23, 4) each tendon 81, that drives the thumb carpometacarpal joint 2's DOF of flexion/extension and abduction/adduction, the ring finger carpometacarpal joint 3's DOF of flexion/extension and the little finger carpometacarpal joint 3's DOF of flexion/extension, is configured to pass a corresponding carpometacarpal joint base's tendon sheath mounting interfaces through the tendon sheath thereof, and is connected to a corresponding carpometacarpal joint rotational end, a tail end of a respective tendon sheath thereof is fixedly connected to the corresponding carpometacarpal joint base's tendon sheath mounting interfaces through the tendon sheath fixing element, 5) the tendons 81, that drives the thumb carpometacarpal joint 2's DOF of circumduction, are fixedly connected to the thumb metacarpal 2's V-shape groove pulley, and the tail ends of the tendon sheaths thereof are fixedly connected to the thumb carpometacarpal joint rotational end 5's tendon sheath mounting interfaces through the tendon sheath fixing element, 6) each tendon 81, that drives a respective finger unit and said respective finger unit's corresponding metacarpophalangeal joints, as well as the respective tendon sheath thereof are configured to pass through the respective finger unit's metacarpal's hand back side and hand palm side respectively, and are configured to be divided into two to three layers by the type III tendon sheath restraint element installed at the respective finger unit's metacarpal's hand back side and hand palm side so as to restrain respective direction and respective curling space of said each tendons and of the respective tendon sheath of said each tendon, 7) the tendons 81, that pass the thumb metacarpal 24, and the tendon sheaths thereof are divided into first inner layers and first outer layer on each side, the tendons 81 on each side's first inner layers are configured to drive the thumb metacarpophalangeal joint 32's DOF of flexion/extension, and are fixedly connected to a thumb metacarpophalangeal joint 32's flexion/extension rotational end, the tail ends of the tendon sheaths thereof are fixedly connected to the thumb metacarpal 24, the tendons 81 on each side's first outer layers are configured to drive the thumb distal joint 1's DOF of flexion/extension, and are configured to continue to extend towards the thumb proximal phalange 11 along with the tendon sheaths thereof, directions of said tendons and tendon sheaths thereof are restrained by small joint's tendon sheath flexible restraint elements when said tendons and tendon sheaths thereof are passing the thumb metacarpophalangeal joint 32, said tendons 81 are fixedly connected to the thumb distal joint 1's interphalangeal joint rotational end 18, the tail ends of the tendon sheaths thereof are fixedly connected to the thumb distal joint 1's interphalangeal joint base 17 through the tendon sheath fixing element, 8) the tendons 81, that pass the index finger metacarpal 25, the middle finger metacarpal 26, the ring finger metacarpal 27, and the little finger metacarpal 28, and the tendon sheaths thereof are divided into second inner layers, second middle layers and second outer layer on each side, the tendons 81 on each side's second inner layers are configured to drive the respective finger unit's finger metacarpophalangeal joints DOF of flexion/extension, and are fixedly connected to a metacarpophalangeal joint flexion/extension rotational end, the tail ends of the tendon sheaths thereof are fixedly connected to corresponding finger metacarpal, the tendons 81 on each side's second middle layers and second outer layers are configured to respectively drive the respective finger unit's proximal joint's DOF of flexion/extension and respective finger unit's distal joint's DOF of flexion/extension, and are configured to continue to extend towards the respective finger unit's proximal phalange along with the tendon sheaths thereof, said tendons' directions are restrained by small joint's tendon sheath flexible restraint elements when said tendons are passing the respective finger unit's finger metacarpophalangeal joints, 9) the tendons 81, that drives the index finger unit 2's proximal joint's DOF of flexion/extension, the middle finger unit's proximal joint's DOF of flexion/extension, the ring finger unit's proximal joint's DOF of flexion/ extension, and the little finger unit's proximal joint's flexion/extension, and the tendon sheaths thereof are configured to pass the respective finger unit's proximal phalange' hand back side and hand palm side, said tendons 81 are fixedly connected to the respective finger unit's proximal joint's interphalangeal joint rotational end 18, the tail ends of the tendon sheaths thereof are fixedly connected to the respective finger unit's proximal joint's interphalangeal joint base 17 through the tendon sheath fixing element, and when the tendons 81, that drive the index finger unit's distal joint's flexion/extension, the middle finger unit's distal joint's DOF of flexion/extension, the ring finger unit's distal joint's DOF of flexion/extension, and the little finger unit's distal joint's flexion/extension, and the tendon sheaths thereof are passing the respective finger unit's proximal phalanges, directions of said tendons and of the tendon sheaths thereof are restrained by the type IV tendon sheath restraint element fixed to the respective finger unit's proximal phalange' hand back side and hand palm side, said tendons and the tendon sheaths thereof are configured to slide along the axis of the type IV tendon sheath restraint element, when said tendons and the tendon sheaths thereof are passing the respective finger unit's proximal joint, directions of said tendons and of the tendon sheaths thereof are restrained by the small joint's tendon sheath restraint element, said tendons are fixedly connected to the respective finger unit's distal joint's interphalangeal joint rotational end 18, the tail ends of the tendon sheaths thereof are fixedly connected to the respective finger unit's distal joint's interphalangeal joint base 17 through the tendon sheath fixing element.

Each joint of the dexterous hand mimics the human hand by the position of the degree axis, and the movement form is close to the human hand, and can be well qualified for operations that the human hand can perform.

Referring to FIGS. 1 and 13, the structure of the hand module is endoskeletal, with sufficient space on the outer surface. The dexterous hand is covered by a bionic skin, a flexible jacket, or a rigid shell with a certain thickness, which is used to protect the internal structure and make the dexterous hand suitable for grasping and automatically adapting to complex curved objects. The bionic skin 91 or the flexible coat can be made of silica gel material.

The outer part of endoskeleton distal phalange 86 has enough space to cover bionic skin 91, flexible coat and rigid shell. Tactile sensors 85 are distributed on the bionic skin 91 to provide tactile feedback, so that the dexterous hand is suitable for grasping and automatically adapting to complex curved objects. The tactile sensor 85 can be made of a strain material (such as a miniature strain gauge).

The rigid shell may be flexible or rigid. The rigid shell is configured to cover the dexterous hand in segments according to the phalanges of each finger unit, the palm unit 6, the wrist module 7, and the forearm module 8.

The bionic skin 91 or the flexible jacket is configured to cover the dexterous hand as a whole, or cover in accordance with the whole of each finger unit or each phalange of the finger unit, the palm unit 6, the wrist module 7, and the forearm module 8 in sections.

The bionic skin 91, the flexible jacket, the rigid shell are made of materials that are waterproof and dustproof and chemical erosion prevention, and each comprises an electromagnetic shielding layer, and/or a protective layer that shields or attenuates ionizing radiation.

It will be appreciated that in the present invention, the hand module of the proposed dexterous hand may have one or more figure units. The number of the finger units may be one, two, three, four, or more than five. Each finger unit may comprise a plurality of phalanges and one or more interphalangeal joints.

The above are only optional embodiments of this application and are not intended to limit this application. This application is subject to various changes and variations for those skilled in the field. Any modification, equivalent replacement, improvement etc. made in the spirit and principle of this application shall be included in the scope of claims of this application.

What is claimed is:

1. A dexterous hand, comprising a hand module,
   wherein the hand module comprises one or more finger units and a palm unit,
   wherein each finger unit comprises a plurality of phalanges and one or more interphalangeal joints,
   wherein the palm unit comprises a carpometacarpal base, one or more metacarpals, one or more carpometacarpal joints, and one or more metacarpophalangeal joint,
   wherein each finger unit is hinged to a respective metacarpal by a respective metacarpophalangeal joint,
   wherein each metacarpal is respectively connected to the carpometacarpal base,
   wherein each interphalangeal joint has degrees of freedom of flexion extension, wherein each metacarpophalangeal joint has degrees of freedom of flexion extension, degrees of freedom of abduction adduction and degrees of freedom of circumduction,
   wherein each interphalangeal joint's degrees of freedom of flexion extension, each metacarpophalangeal joint's degrees of freedom of flexion extension, each metacarpophalangeal joint's degrees of freedom of abduction adduction are driven by different actuators.

2. The dexterous hand of claim 1 further comprising a wrist module, wherein the wrist module comprises a wrist joint, wherein the hand module is connected to the wrist module,
   wherein the wrist joint has degrees of freedom of flexion extension, and degrees of freedom of abduction adduction,
   wherein each interphalangeal joint's degrees of freedom of flexion extension and each metacarpophalangeal joint's degrees of freedom of flexion extension and the wrist joint's degrees of freedom of flexion extension and degrees of freedom of abduction adduction each is respectively driven by an antagonistic drive mechanism comprising a pair of first actuators, wherein the antagonistic drive mechanism adopts tendon transmission, wherein the dexterous hand's one or more tendons are covered with a plurality of tendon sheaths that protect and guide the tendons.

3. The dexterous hand of claim 2, wherein each metacarpophalangeal joint has degrees of freedom of circumduction, wherein each metacarpophalangeal joint's degrees of freedom of circumduction is a passive degrees of freedom driven by external forces.

4. The dexterous hand of claim 3, wherein the metacarpophalangeal joint each is respectively configured to adopt a 3-degree-of-freedom metacarpophalangeal joint universal module, wherein the 3-degree-of-freedom metacarpophalangeal joint universal module has degrees of freedom of flexion extension, degrees of freedom of abduction adduction, and degrees of freedom of circumduction, wherein the axes of said degrees of freedom of flexion extension, degrees of freedom of abduction adduction, and degrees of freedom of circumduction are orthogonal, wherein the 3-degree-of-freedom metacarpophalangeal joint universal module comprises a metacarpophalangeal joint abduction adduction rotational end, a metacarpophalangeal joint abduction adduction shaft, a metacarpophalangeal joint flexion extension rotational end, a metacarpophalangeal joint flexion extension shaft, metacarpophalangeal joint flexion extension angle sensor, metacarpophalangeal joint abduction adduction angle sensor, metacarpophalangeal joint circumduction angle sensor, and a metacarpophalangeal joint tendon guide groove, wherein the surface of the metacarpophalangeal joint abduction adduction shaft has a gap to fix with and fit with the metacarpophalangeal joint flexion extension shaft, and an end thereof has a first interface adapted to the metacarpophalangeal joint abduction adduction angle sensor, wherein the surface of the metacarpophalangeal joint flexion extension shaft has a gap to fix with and fit with the metacarpophalangeal joint abduction adduction shaft, and an end thereof has a second interface adapted to the metacarpophalangeal joint flexion extension angle sensor, wherein the metacarpophalangeal joint flexion extension rotational end comprises a circumduction joint base that supports the finger unit to perform circumduction motion and bears force, and wherein the metacarpophalangeal joint tendon guide groove is fixedly connected to the metacarpophalangeal joint abduction adduction rotational end, and tendon and the tendon sheaths passing the metacarpophalangeal joint adhere to the metacarpophalangeal joint tendon guide groove to slide, wherein the lateral section of the metacarpophalangeal joint tendon guide groove is semicircular.

5. The dexterous hand of claim 4, wherein the 3-degree-of-freedom metacarpophalangeal joint universal module comprises a circumduction reset device wherein the circumduction reset device is installed at the circumduction joint base of the metacarpophalangeal joint flexion extension rotational end, and comprises an elastic reset element, so that the finger units perform the circumduction motion when subjected to external torsion, and wherein the amplitude of the circumduction motion is positively related to said external torsion, and wherein when the external torsion disappears, the finger units return to original position thereof, and wherein the circumduction reset device has a third interface for installing a strain gauge or the joint force and torque sensor.

6. The dexterous hand of claim 2, wherein each metacarpophalangeal joint's degrees of freedom of abduction adduction is driven by respective second actuators.

7. The dexterous hand of claim 6, wherein the first actuators and the second actuators are configured as rotary actuators, wherein each first actuators' output shaft is equipped with a respective capstan.

8. The dexterous hand of claim 7, wherein the dexterous hand's one or more capstans are equipped with torque sensors to measure the torque in the capstan acted by each first actuator's output shaft.

9. The dexterous hand of claim 6, wherein each metacarpal is respectively installed with second actuator, wherein the second actuators are palm-internal actuator.

10. The dexterous hand of claim 6, wherein an improved solution is that each second actuator is configured to use linear actuators, and to drive a respective metacarpophalangeal joint through a hinged linkage mechanism to perform abduction adduction motion.

11. The dexterous hand of claim 2, wherein the rotational end of a controlled joint is fixedly connected to any point on the tendon through a tendon fixing element, wherein the controlled degrees of freedom of the controlled joint is jointly driven by the pair of first actuators.

12. The dexterous hand of claim 2, wherein the finger units comprise a thumb unit; an index finger unit; a middle finger unit, a ring finger unit; a little finger unit;

wherein the metacarpals comprise a thumb metacarpal; an index finger metacarpal; a middle finger metacarpal; a ring finger metacarpal; a little finger metacarpal, wherein the carpometacarpal joints comprise a thumb carpometacarpal joint; a ring finger carpometacarpal joint; and a little finger carpometacarpal joint, wherein the thumb metacarpal is hinged to the carpometacarpal base through the thumb carpometacarpal joint, wherein the index finger metacarpal is fixed to the carpometacarpal base, wherein the middle finger metacarpal is fixed to the carpometacarpal base, wherein the ring finger metacarpal is hinged to the carpometacarpal base through the ring finger carpometacarpal joint, and wherein the little finger metacarpal is hinged to the carpometacarpal base through the little finger carpometacarpal joint.

13. The dexterous hand of claim 12, wherein the thumb carpometacarpal joint has degrees of freedom of circumduction, degrees of freedom of flexion extension and abduction adduction, and wherein the thumb carpometacarpal joint's degrees of freedom of circumduction, degrees of freedom of flexion extension and abduction adduction are respectively driven by the antagonistic drive mechanism comprising the pair of first actuators, wherein the antagonistic drive mechanism adopts tendon transmission.

14. The dexterous hand of claim 12, wherein the ring finger carpometacarpal joint has degrees of freedom of flexion extension, and degrees of freedom of adduction/abduction, wherein the little finger carpometacarpal joint has degrees of freedom of flexion extension, and degrees of freedom of adduction/abduction, wherein degrees of freedom of adduction/abduction of the ring finger carpometacarpal joint and degrees of freedom of adduction/abduction of the little finger carpometacarpal joint are passive degrees of freedom driven by external forces, wherein the ring finger carpometacarpal joint's degrees of freedom of flexion extension and the little finger carpometacarpal joint's degrees of freedom of flexion extension are respectively driven by the antagonistic drive mechanism comprising the pair of first actuators, wherein the antagonistic drive mechanism adopts tendon transmission.

15. The dexterous hand of claim 12, wherein the thumb unit comprises a thumb distal phalange; a thumb proximal phalange; and a thumb distal joint, wherein the index finger unit comprises an index finger distal phalange; an index finger middle phalange; an index finger proximal phalange; an index finger distal joint; and an index finger proximal joint, wherein the middle finger unit comprises a middle finger distal phalange; a middle finger middle phalange; a middle finger proximal phalange; a middle finger distal joint; and a middle finger proximal joint, wherein the ring finger unit comprises a ring finger distal phalange; a ring finger middle phalange; a ring finger proximal phalange; a ring finger distal joint; and a ring finger proximal joint, wherein the little finger unit comprises a little finger distal phalange; a little finger middle phalange; a little finger proximal phalange; a little finger distal joint; and a little finger proximal joint, and wherein the metacarpophalangeal joints comprise a thumb metacarpophalangeal joint; an index finger metacarpophalangeal joint; a middle finger metacarpophalangeal joint; a ring finger metacarpophalangeal joint; and a little finger metacarpophalangeal joint.

16. The dexterous hand of claim 15, wherein the length ratio of the phalanges of the thumb unit, the index finger unit, the middle finger unit, the ring finger unit and the little finger unit are configured to simulate human hands.

17. The dexterous hand of claim 12, wherein main axes of the index finger metacarpal and the middle finger metacarpal are configured to form an included angle of 0 to 15 degrees.

18. The dexterous hand of claim 12, wherein the thumb metacarpal's root is configured to cooperate with the thumb carpometacarpal joint to form a first evolute pair with degrees of freedom of flexion extension and abduction adduction, and is fixed to a V-shape groove pulley used for the tendon transmission, wherein degrees of freedom of flexion extension and abduction adduction of the thumb carpometacarpal joint is 1-degree-of-freedom, and couples degrees of freedom of flexion extension and degrees of freedom of abduction adduction, wherein the axis of degrees of freedom of flexion extension and abduction adduction of the thumb carpometacarpal joint and the axis of degrees of freedom of abduction adduction of the thumb metacarpophalangeal joint are configured to form an included angle of 30 to 60 degrees, wherein the thumb carpometacarpal joint comprises a thumb carpometacarpal joint base, a thumb carpometacarpal joint rotational end, thumb carpometacarpal joint circumduction angle sensor, and thumb carpometacarpal joint flexion extension and abduction adduction angle sensor, wherein an end of the thumb carpometacarpal joint rotational end and the thumb carpometacarpal joint base form a revolute pair with degrees of freedom of circumduction, and is coaxially fixed with a V-shape groove pulley used for tendon transmission, wherein an opposite end of the thumb carpometacarpal rotational end and the thumb metacarpal form a second evolute pair with degrees of freedom of flexion extension and abduction adduction, and wherein the thumb carpometacarpal joint rotational end comprises the tendon sheath mounting interfaces.

19. The dexterous hand of claim 12, wherein the palm unit comprises a ring finger metacarpal flexible constraint element and a little finger metacarpal flexible constraint element, wherein the ring finger metacarpal flexible constraint element is configured to flexibly couple the middle finger metacarpal with the ring finger metacarpal, wherein the little finger metacarpal flexible constraint element is configured to flexibly couple the ring finger metacarpal with the little finger metacarpal, wherein the ring finger metacarpal flexible constraint element is configured to restrain movement range of the ring finger metacarpal, and to keep the ring finger metacarpal in a resting position when there is no external force, wherein when the ring finger metacarpal is performing flexion movement, the ring finger metacarpal flexible constraint element holds the ring finger metacarpal and adduction motion occurs incidentally, wherein the little finger metacarpal flexible constraint element is configured to restrain movement range of the little finger metacarpal, and to keep the little finger metacarpal in a resting position when there is no external force, wherein when the little finger metacarpal is performing flexion movement, the little finger metacarpal flexible constraint element holds the little finger metacarpal and the adduction motion occurs incidentally, and wherein when the palm unit is subjected to external forces from little finger side to thumb side, the adduction motion of the ring finger metacarpal and the little finger metacarpal can occur simultaneously, and the ring finger metacarpal flexible constraint element and the ring finger metacarpal flexible constraint element absorbs and cushions said external forces.

20. The dexterous hand of claim 12, wherein the ring finger carpometacarpal joint comprises a ring finger carpometacarpal joint base, a ring finger carpometacarpal rotational end, ring finger carpometacarpal joint rotation angle sensor, ring finger carpometacarpal joint abduction adduction angle sensor, wherein the little finger carpometacarpal joint comprises a little finger carpometacarpal joint base, a little finger carpometacarpal rotational end, little finger carpometacarpal joint rotation angle sensor, little finger carpometacarpal joint abduction adduction angle sensor.

21. The dexterous hand of claim 2, wherein speed and output force of the first actuators that constitute the antagonistic drive are used to control one or more of motion, torque, joint damping and joint stiffness of the controlled joint.

22. The dexterous hand of claim 2, wherein the dexterous hand's one or more tendons are provided with tendon tension sensors.

23. The dexterous hand of claim 2, wherein the joint base of each joint, which uses the tendon transmission, of the dexterous hand has respective tendon sheath mounting interfaces.

24. The dexterous hand of claim 2, wherein the axis of the wrist joint's degrees of freedom of abduction adduction and the axis of the wrist joint's degrees of freedom of flexion extension are orthogonal, wherein the wrist joint comprises a wrist joint abduction adduction rotational end, a wrist joint abduction adduction shaft, a wrist joint flexion extension rotational end, a wrist joint flexion extension shaft, wrist joint abduction adduction angle sensor, wrist joint flexion extension angle sensor and a wrist joint tendon guide groove, wherein an end of the wrist joint abduction adduction shaft is provided with a coaxial driven V-shape groove pulley, a middle part of the wrist joint abduction adduction shaft has a gap for locking and matching with the wrist joint flexion extension shaft, and an opposite end of the wrist joint abduction adduction shaft comprises a first interface adapted to the wrist joint abduction adduction angle sensor, wherein the surface of the wrist joint flexion extension shaft has a gap to fix with and fit with the wrist joint abduction adduction shaft, and an end thereof comprises a second interface adapted to the wrist joint flexion extension angle sensor, wherein the wrist joint flexion extension rotational end comprises a third interface connected with the carpometacarpal base, and a fourth interface for installing the joint force and torque sensor, wherein the wrist joint tendon guide groove is fixedly connected to the wrist joint abduction adduction rotational end, and the tendon driving the wrist joint's degrees of freedom of flexion extension adheres to the wrist joint tendon guide groove to slide; the side section of the wrist joint tendon guide groove is semi-circular.

25. The dexterous hand of claim 2 further comprising a forearm module, wherein the wrist module is connected to the forearm module, wherein the first actuators are installed in the forearm module to serve as the forearm-internal actuators, wherein the wrist module comprises a wrist support frame that is fixed to the forearm module, wherein the carpometacarpal base is hinged to the wrist support frame through the wrist joint, and wherein the wrist support frame comprises the tendon sheath mounting interfaces, a wrist joint base, and a forearm mounting base.

26. The dexterous hand of claim 25, wherein the forearm module comprises a actuator storage bin, wherein a plurality of the forearm-internal actuators are installed in the actuator storage bin, wherein the layout of some or all of the forearm-internal actuators in the forearm module includes one or more of:

installing some or all of the forearm-internal actuators in multiple rows from the thumb side to the little finger side; and/or installing some or all of the forearm-internal actuators in multiple rows from the hand side to the elbow side; and/or dividing some or all of the forearm-internal actuators into a plurality of pairs, wherein each pair is configured to drive a respective degree of freedom to form the antagonistic drive, wherein a mounting method for each pair comprises:

installing the respective forearm-internal actuators of each pair in the opposite direction, wherein the respective forearm-internal actuators comprise a respective first shaft forearm-internal actuator and a respective second forearm-internal actuator, wherein the respective first shaft forearm-internal actuator's output shaft is facing hand back side and the respective second shaft inner output shaft's output shaft is facing hand palm side; or installing the respective forearm-internal actuators of each pair in the opposite direction, wherein the respective first shaft forearm-internal actuator's output shaft is facing the thumb side of the hand and the respective second shaft inner output shaft's output shaft is facing the little finger side; or installing the respective forearm-internal actuators of each pair in the same direction, with the respective forearm-internal actuator's output shaft facing the hand back side; or installing the respective forearm-internal actuators of each pair in the same direction, with the respective forearm-internal actuator's output shaft facing the hand palm side; or installing the respective forearm-internal actuators of each pair in the same direction, with the respective forearm-internal actuator's output shaft facing the thumb side; or installing the respective forearm-internal actuators of each pair in the same direction, with the respective forearm-internal actuator's output shaft facing the little finger side.

27. The dexterous hand of claim 25, wherein the forearm-internal actuator's output shaft is installed with capstans, wherein the forearm module's capstans each has one or more diameters, and each of the forearm module's capstans is respectively distributed on the forearm module's hand back side, forearm module's hand palm side, forearm module's thumb side, or the forearm module's little finger side, and wherein some or all of the capstans on each side are divided into one to multiple layers.

28. The dexterous hand of claim 25, wherein the forearm module comprises a tendon sheath guide base, wherein the tendon sheath guide base is installed at the junction of the wrist support frame and the forearm module, wherein the tendon sheath guide base comprises a plurality of tendon sheath mounting interfaces, wherein an end of each tendon sheath is fixed with a tendon-driven joint's joint base, and an opposite end is fixed with the tendon sheath mounting interfaces of the tendon sheath guide base.

29. The dexterous hand of claim 28, wherein the plurality of tendon sheath mounting interfaces of the tendon sheath guide base are respectively distributed on the hand back side and the palm side of the tendon sheath guide, wherein the plurality of tendon sheath mounting interfaces on each side are arranged in one to multiple layers, and wherein the tendon sheath guide has a first interface adapted to the wrist support frame and a second interface adapted to the forearm module.

30. The dexterous hand of claim 28, wherein the one or more tendon sheaths of the dexterous hand are respectively mounted at the end of each tendon sheath by a detachable tendon sheath fixing element on the tendon sheath mounting interfaces of the tendon sheath guide base, and wherein the one or more tendon sheaths of the dexterous hand are respectively mounted at the opposing end of each tendon sheath on the tendon sheath mounting interfaces of the joint base of the joints using tendon transmission through the detachable tendon sheath fixing element.

31. The dexterous hand of claim 28 wherein the tendon's part, which is between the actuators and the tendon sheath guide, is provided with a tendon coupling, wherein the tendon coupling can be disconnected or coupled so that the tendon is disconnected or coupled from the middle of the tendon, and wherein the maximum outer diameter of the tendon coupling is smaller than the inner diameter of each tendon sheath mounting interface of the tendon sheath guide base.

32. The dexterous hand of claim 28, wherein the dexterous hand is configured to adopt a tendon transmission layout comprising:

distributing a plurality of the tendons on the dexterous hand's hand back side and hand palm side, wherein an end of the plurality of the tendons is fixedly connected to corresponding first actuators' output shafts or capstans, wherein a starting end of the tendon sheath of the plurality of the tendons is fixed to the tendon sheath mounting interfaces on the tendon sheath guide base's hand back side and hand palm side through a tendon sheath fixing element, respectively, wherein the plurality of the tendons are passing through said tendon sheath mounting interfaces and extend towards the wrist module, wherein the tendons, that drive the wrist joint, are configured to pass the wrist support framework's tendon sheath mounting interfaces through the tendon sheaths thereof, wherein the tendons that drive the wrist joint are respectively connected to a wrist joint abduction adduction rotational end and a wrist joint flexion extension rotational end, wherein the tail ends of the tendon sheaths thereof are fixedly connected to the wrist support framework's tendon sheath mounting interfaces through the tendon sheath fixing element, wherein other tendons and the tendon sheaths thereof are configured to pass the wrist joint at the dexterous hand's hand back side and hand palm side respectively, and directions and curling spaces of said other tendons and of the tendon sheaths of said other tendons are restrained by large joint's tendon sheath flexible restraint elements installed at the wrist module, wherein said other tendons and the tendon sheaths thereof are then configured to converge at the carpometacarpal base's hand back side and hand palm side, wherein each tendon, that drives the thumb carpometacarpal joint's degrees of freedom of flexion extension and abduction adduction, the ring finger carpometacarpal joint's degrees of freedom of flexion extension and the little finger carpometacarpal joint's degrees of freedom of flexion extension, is configured to pass a corresponding carpometacarpal joint base's tendon sheath mounting interfaces through the tendon sheath thereof, and is connected to a corresponding carpometacarpal joint rotational end, wherein a tail end of a respective tendon sheath thereof is fixedly connected to the corresponding carpometacarpal joint base's tendon sheath mounting interfaces through the tendon sheath fixing element, wherein the tendons, that drives the thumb carpometacarpal joint's degrees of freedom of circumduction, are fixedly connected to the thumb metacarpal's V-shape groove pulley, and the tail ends of the tendon sheaths thereof are fixedly connected to the thumb carpometacarpal joint rotational end's tendon sheath mounting interfaces through the tendon sheath fixing element, wherein each tendon, that drives a respective finger unit and said respective finger unit's corresponding metacarpophalangeal joints, as well as the respective tendon sheath thereof are configured to pass through the respective finger unit's metacarpal's hand back side and hand palm side respectively, and are configured to be divided into two to three layers by the type III tendon sheath restraint element installed at the respective finger unit's metacarpal's hand back side and hand palm side so as to restrain respective direction and respective curling space of said each tendons and of the respective tendon sheath of said each tendon, wherein the tendons, that pass the thumb metacarpal, and the tendon sheaths thereof are divided into first inner layers and first outer layer on each side, wherein the tendons on each side's first inner layers are configured to drive the thumb metacarpophalangeal joint's degrees of freedom of flexion extension, and are fixedly connected to a thumb metacarpophalangeal joint flexion extension rotational end, the tail ends of the tendon sheaths thereof are fixedly connected to the thumb metacarpal, wherein the tendons on each side's first outer layers are configured to drive the thumb distal joint's degrees of freedom of flexion extension, and are configured to continue to extend towards the thumb proximal phalange along with the tendon sheaths thereof, directions of said tendons and tendon sheaths thereof are restrained by small joint's tendon sheath flexible restraint elements when said tendons and tendon sheaths thereof are passing the thumb metacarpophalangeal joint, wherein said tendons are fixedly connected to the thumb distal joint's interphalangeal joint rotational end, wherein the tail ends of the tendon sheaths thereof are fixedly connected to the thumb distal joint's interphalangeal joint base through the tendon sheath fixing element, wherein the tendons, that pass the index finger metacarpal, the middle finger metacarpal, the ring finger metacarpal, and the little finger metacarpal, and the tendon sheaths thereof are divided into second inner layers, second middle layers and second outer layer on each side, wherein the tendons on each side's second inner layers are configured to drive the respective finger unit's finger metacarpophalangeal joints degrees of freedom of flexion extension, and are fixedly connected to a metacarpophalangeal joint flexion extension rotational end, wherein the tail ends of the tendon sheaths thereof are fixedly connected to corresponding finger metacarpal, wherein the tendons on each side's second middle layers and second outer layers are configured to respectively drive the respective finger unit's proximal joint's degrees of freedom of flexion extension and respective finger unit's distal joint's degrees of freedom of flexion extension, and are configured to continue to extend towards the respective finger unit's proximal phalange along with the tendon sheaths thereof, wherein said tendons' directions are restrained by the small joint's tendon sheath flexible restraint elements when said tendons are passing the respective finger unit's finger metacarpophalangeal joints, wherein the tendons, that drives the index finger unit's proximal joint's degrees of freedom of flexion extension, the middle finger unit's proximal joint's degrees of freedom of flexion extension, the ring finger unit's proximal joint's degrees of freedom of flexion extension, and the little finger unit's proximal joint's flexion extension, and the tendon sheaths thereof are configured to pass the respective finger unit's proximal phalange' hand back side and hand palm side, wherein said tendons are fixedly connected to the respective finger unit's proximal joint's interphalangeal joint rotational end, wherein the tail ends of the tendon sheaths thereof are fixedly connected to the respective finger unit's proximal joint's interphalangeal joint base through the tendon sheath fixing element, and wherein when the tendons, that drive the index finger unit's distal joint's flexion extension, the middle finger unit's distal joint's degrees of freedom of flexion extension, the ring finger unit's distal joint's degrees of freedom of flexion extension, and the little finger unit's distal joint's flexion extension, and the tendon sheaths thereof are passing the respective finger unit's proximal phalanges, directions of said tendons and of the tendon sheaths thereof are restrained by the type IV tendon sheath restraint element fixed to the respective finger unit's proximal phalange' hand back side and hand palm side, wherein said tendons and the tendon sheaths thereof are configured to slide along the axis of the type IV tendon sheath restraint element, when said tendons and the tendon sheaths thereof are passing the respective finger unit's proximal joint, directions of said tendons and of the tendon sheaths thereof are restrained by the small joint's tendon sheath restraint element, wherein said tendons are fixedly connected to the respective finger unit's distal joint's interphalangeal joint rotational end, wherein the tail ends of the tendon sheaths thereof are fixedly connected to the respective finger unit's distal joint's interphalangeal joint base through the tendon sheath fixing element.

33. The dexterous hand of claim 2, wherein an improved solution is that each first actuator is configured to use linear actuators, and each forearm-internal actuator's output shaft is fixedly connected to the tendon.

34. The dexterous hand of claim 2, wherein another improved solution is that each first actuator is configured to use rotary actuators, a lead screw mechanism is used to convert the rotary motion of each forearm-internal actuator's output shaft into a linear motion, each forearm-internal actuator's output shaft is fixedly connected to the lead screw rod, and the screw mechanism's linear motion end of is fixed to the tendon.

35. The dexterous hand of claim 34, wherein the actuator storage bin comprises one or more sub storage bins, wherein if the number of the sub storage bins is more than one, sub storage bins can be disassembled or assembled with each other.

36. The dexterous hand of claim 2, wherein the interphalangeal joints and the metacarpophalangeal joint each comprises a type I tendon sheath restraint element, wherein the wrist joint is equipped with a type II tendon sheath restraint element, wherein the metacarpals each is equipped with a type III tendon sheath restraint element on the upper surface and the lower surface thereof, wherein a type IV tendon sheath restraint element is installed on each of the proximal phalanges' hand back side and hand palm side, wherein the type I tendon sheath restraint element is a first flexible element that can flex, and comprises one or more type I tendon sheath restraint element's guide grooves or first guide holes for guiding one to four of the tendon sheaths to slide along respective axes thereof, wherein the type II tendon sheath restraint element is a second flexible element that can flex, comprises one or more type II tendon sheath restraint element's guide grooves or guide holes for guiding at least five of the tendon sheaths to slide along respective axes thereof, and has a structure allowing one or more of the tendon sheaths that pass through the type II tendon sheath restraint element to curl respectively inside the type II tendon sheath restraint element, wherein the type III tendon sheath restraint element comprises one or more type III tendon sheath restraint element's guide grooves or guide holes for guiding one or more of the tendon sheaths to slide along respective axes thereof, and has a structure allowing one or more of the tendon sheaths that pass through the type III tendon sheath restraint element to curl respectively inside the type II tendon sheath restraint element, and wherein the type IV tendon sheath restraint element comprises one or more type IV tendon sheath restraint element's guide grooves or guide holes for guiding one or more of the tendon sheaths to slide along respective axes thereof.

37. The dexterous hand of claim 2, wherein the dexterous hand is covered by a bionic skin, a flexible jacket, or a rigid shell, wherein the bionic skin, the flexible jacket, and the rigid shell are made of materials that are waterproof and dustproof and chemical erosion prevention, and each comprises an electromagnetic shielding layer, and/or a protective layer that shields or attenuates ionizing radiation.

38. The dexterous hand of claim 37, wherein the rigid shell is configured to cover the dexterous hand in segments according to the phalanges of each finger unit, the palm unit, and the wrist module, wherein the bionic skin or the flexible jacket is configured to cover the dexterous hand as a whole, or cover in accordance with the whole of each finger unit or each phalange of the finger unit, the palm unit, and the wrist module in sections.

39. The dexterous hand of claim 1, wherein joint angle sensor is installed at each joint of the dexterous hand to measure the rotation angle and angular velocity of each degree of freedom.

40. The dexterous hand of claim 1, wherein joint force and torque sensors are installed at all or part of the joints of the dexterous hand.

41. The dexterous hand of claim 40, wherein the phalanges comprise distal phalanges, wherein the distal phalanges each is configured as a hollow structure, wherein the hollow structure is configured to accommodate the joint force and torque sensors as well as circuit and signal lines.

42. The dexterous hand of claim 40, wherein the phalanges comprise middle phalanges, wherein the middle phalanges each is configured as a hollow tube, and wherein the hollow tube is configured to accommodate the joint force and torque sensors as well as circuit and signal lines.

43. The dexterous hand of claim 40, wherein the phalanges comprise proximal phalanges, wherein the proximal phalanges each is configured as a hollow tube, and wherein the hollow tube is configured to accommodate a circumduction reset device, the joint force and torque sensors as well as the circuit and signal lines.

44. The dexterous hand of claim 1, wherein the phalanges are configured with light alloy or light non-metallic material with electromagnetic shielding layers.

45. The dexterous hand of claim 1, wherein the interphalangeal joint each is respectively configured to use a 1-degree-of-freedom interphalangeal joint universal module, wherein the 1-degree-of-freedom interphalangeal joint universal module has degrees of freedom of flexion extension, and comprises an interphalangeal joint base, an interphalangeal joint rotational end, an interphalangeal joint flexion extension shaft, and interphalangeal joint flexion extension angle sensor, wherein the interphalangeal joint flexion extension shaft has one or more first interfaces adapted to the interphalangeal joint flexion extension angle sensor and one or more second interfaces to lock with the interphalangeal joint rotational end, wherein the interphalangeal joint base and the interphalangeal joint rotational end each has a respective mounting interface for mounting the phalanges or the joint force and torque sensors.

46. The dexterous hand of claim 1, wherein the structure of the hand module is endoskeletal.

* * * * *